United States Patent
Janik et al.

(10) Patent No.: US 10,756,043 B2
(45) Date of Patent: Aug. 25, 2020

(54) METHOD OF FABRICATING IMPLANTABLE MEDICAL DEVICES FROM A POLYMER COUPON THAT IS BONDED TO A RIGID SUBSTRATE

(71) Applicant: Stryker Corporation, Kalamazoo, MI (US)

(72) Inventors: John Janik, Hudsonville, MI (US); Robert Brindley, Delton, MI (US); Edward Chia-Ning Tang, Ann Arbor, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/643,656

(22) Filed: Jul. 7, 2017

(65) Prior Publication Data

US 2017/0367652 A1 Dec. 28, 2017

Related U.S. Application Data

(60) Continuation of application No. 14/615,547, filed on Feb. 6, 2015, now Pat. No. 9,700,262, which is a
(Continued)

(51) Int. Cl.
*A61B 5/04* (2006.01)
*H01L 23/00* (2006.01)
(Continued)

(52) U.S. Cl.
CPC ............... *H01L 24/19* (2013.01); *A61B 5/05* (2013.01); *A61N 1/05* (2013.01); *A61N 1/0553* (2013.01); *H01L 23/5389* (2013.01); *A61B 5/04* (2013.01)

(58) Field of Classification Search
CPC .......... A61B 5/04; A61B 5/05; A61B 5/6832; A61N 1/05; A61N 1/0553; H01L 23/5389;
(Continued)

(56) References Cited

U.S. PATENT DOCUMENTS 6,075,180 A * 6/2000 Sharber .................. C09J 5/06
623/11.11
6,304,784 B1 10/2001 Allee et al.
(Continued)

FOREIGN PATENT DOCUMENTS

DE  10 2005 061 769 A1  6/2007
EP   1 883 107 A2       1/2008
WO  2008/080073 A2      7/2008

OTHER PUBLICATIONS

Bulcke, et al., "Active Electrode Arrays by chip Embedding in a Flexible Silicone Carrier", 28th IEEE EMBS Annual International Conference, Aug. 30, 2006.
(Continued)

*Primary Examiner* — Lan Vinh
(74) *Attorney, Agent, or Firm* — Howard & Howard Attorneys PLLC

(57) ABSTRACT

Plural medical device formed from one or more layers of thin film polymer are assembled from a single polymer coupon. Initially the coupon is bonded to a rigid substrate. Force, heat and a suction are selectively applied to the coupon to ensure that it has a consistent height across its exposed surface. Once the polymer coupon is bonded the components forming the medical device are attached to the coupon and the coupon is shaped to form the individual medical devices. Shaped sections of the coupon are then lifted off the rigid backing. The lifted off sections on which the components were attached are the medical devices.

13 Claims, 31 Drawing Sheets

Related U.S. Application Data division of application No. 14/080,259, filed on Nov. 14, 2013, now Pat. No. 8,951,426, which is a continuation of application No. PCT/US2012/037888, filed on May 15, 2012.

(60) Provisional application No. 61/486,906, filed on May 17, 2011.

(51) Int. Cl.
*A61N 1/05* (2006.01)
*H01L 23/538* (2006.01)
*A61B 5/05* (2006.01)

(58) Field of Classification Search
CPC . H01L 24/19; H01L 21/0272; H01L 21/0331; H01L 2224/0347
USPC ...... 216/20, 33, 34, 35, 40, 41, 46; 438/106, 438/166, 745, 753
See application file for complete search history.

(56) References Cited

U.S. PATENT DOCUMENTS

| | | | |
|---|---|---|---|
| 7,218,971 B2 | 5/2007 | Heil et al. | |
| 7,877,866 B1 | 2/2011 | Greenberg et al. | |
| 8,209,023 B2 | 6/2012 | Zhou et al. | |
| 8,524,311 B1 | 9/2013 | Greenberg et al. | |
| 8,951,426 B2 * | 2/2015 | Brindley | A61N 1/0553 216/33 |
| 2002/0128700 A1 | 9/2002 | Cross, Jr. | |
| 2003/0108671 A1 * | 6/2003 | Jahromi | C08J 7/065 427/248.1 |
| 2006/0287660 A1 | 12/2006 | Syed et al. | |
| 2007/0087531 A1 | 4/2007 | Kirk | |
| 2008/0177363 A1 | 7/2008 | Schouenborg et al. | |
| 2008/0288037 A1 | 11/2008 | Neysmith et al. | |
| 2009/0124965 A1 | 5/2009 | Greenberg et al. | |
| 2009/0293270 A1 * | 12/2009 | Brindley | A61N 1/05 29/829 |
| 2010/0178722 A1 | 7/2010 | deGraff et al. | |
| 2010/0204560 A1 * | 8/2010 | Salahieh | A61B 5/01 600/373 |
| 2010/0215716 A1 * | 8/2010 | Troxel | A61B 17/7002 424/423 |
| 2010/0331935 A1 * | 12/2010 | Tabada | A61N 1/05 607/116 |
| 2011/0077660 A1 | 3/2011 | Janik et al. | |
| 2011/0237921 A1 * | 9/2011 | Askin, III | A61B 5/0408 600/377 |
| 2012/0022551 A1 | 1/2012 | Staunton et al. | |
| 2012/0310316 A1 | 12/2012 | Janik et al. | |

OTHER PUBLICATIONS

European Patent Office, "ISA Search Report & Written Opion for PCT/US2012/037888".

\* cited by examiner

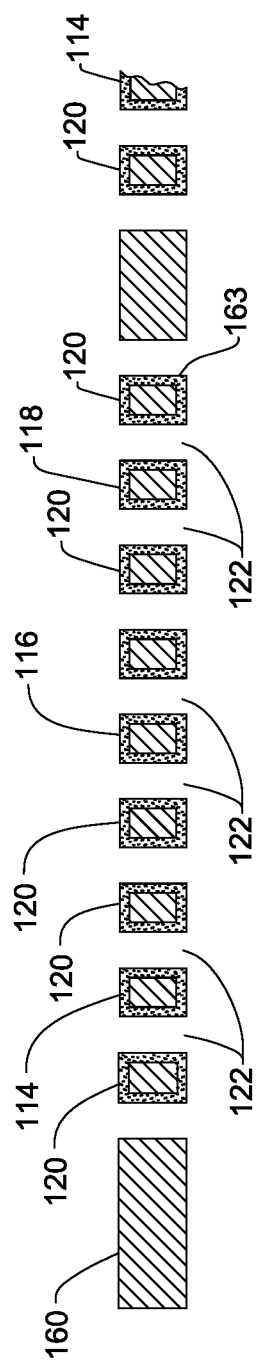

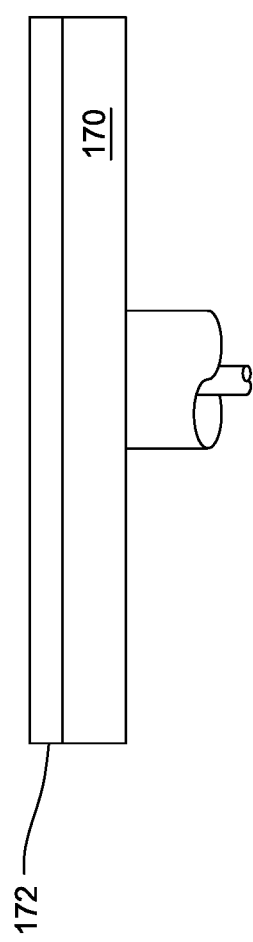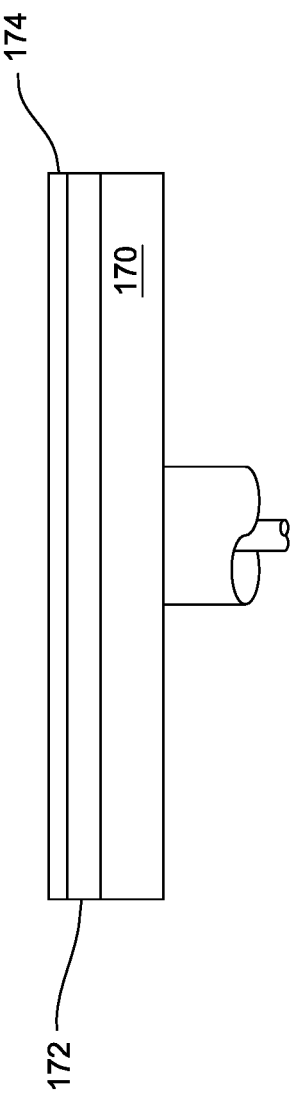

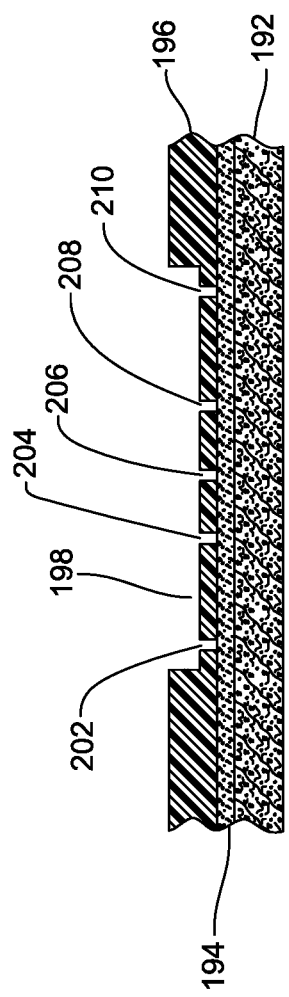
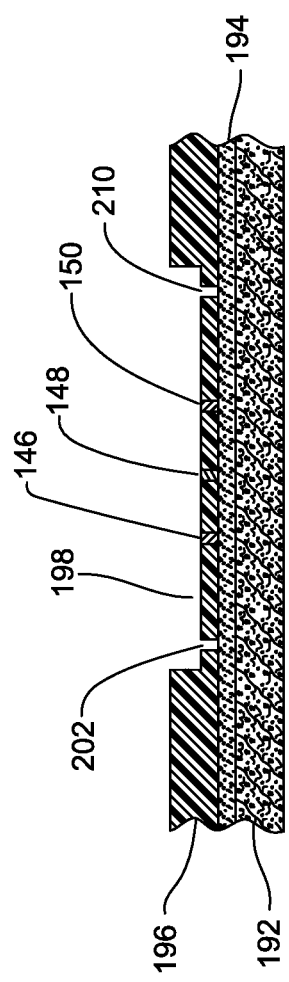

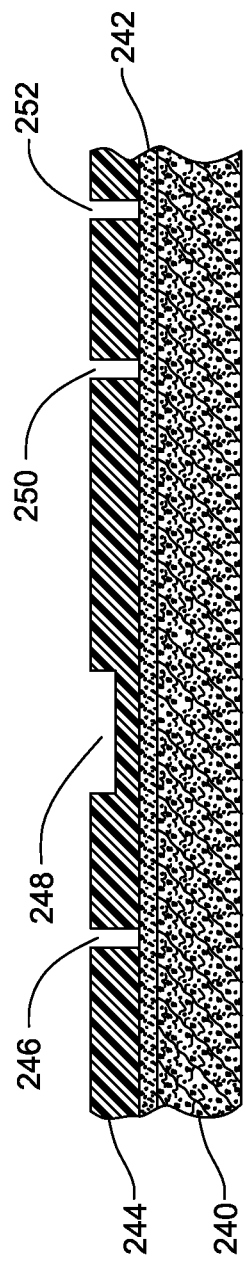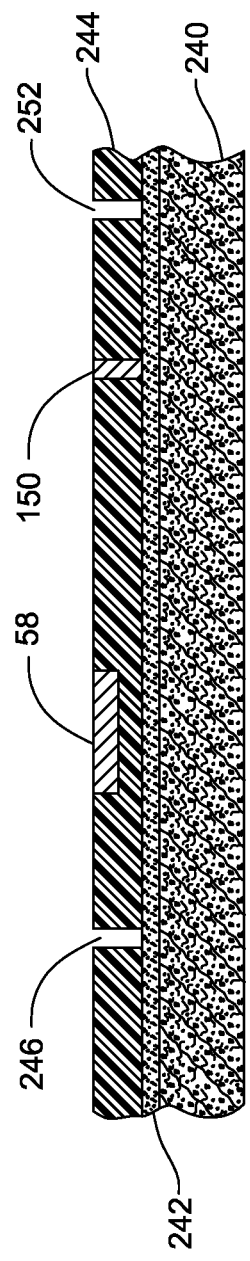

METHOD OF FABRICATING IMPLANTABLE MEDICAL DEVICES FROM A POLYMER COUPON THAT IS BONDED TO A RIGID SUBSTRATE

RELATIONSHIP TO PRIORITY APPLICATIONS

This application is a divisional of U.S. patent application Ser. No. 14/615,547 filed 6 Feb. 2017, now U.S. Pat. No. 9,700,262. Application Ser. No. 14/615,547 is a divisional of U.S. patent application Ser. No. 14/080,259 filed 14 Nov. 2013 now U.S. Pat. No. 8,951,426. Application Ser. No. 14/080,259 is a continuation of PCT App. No. PCT/US2012/037888, filed 15 May 2012, now expired. PCT App. No. PCT/US2012/037888 is a non-provisional of U.S. Prov. Pat. App. No. 61/486,906 filed 17 May 2011, now expired. The contents of the above-identified applications from which this application claims priority are incorporated herein by reference.

FIELD OF THE INVENTION

This invention relates generally to a method of manufacturing implantable medical devices that include a substrate, intermediate layers or a superstrate formed from a thin film polymer. More particularly, this invention relates to a method of manufacturing implantable electrode arrays that includes one or more thin film polymer layers.

BACKGROUND OF THE INVENTION

There is an increasing interest in providing articles of manufacture that include one or more layers support layers formed from a thin film polymer. A "thin film polymer" is understood to be a polymer having a thickness of 1 mm or less. This polymer has found to be a good substrate or carrier layer on which electrically conductive traces can be formed. Also, this polymer, even though thin in cross section, has sufficient mechanical strength that it can also support the mounting of mechanical, electromechanical and electrical components. Another feature of this polymer is that even though it is capable of supporting components and conductors, it is flexible. Thus, this polymer can serve as a substrate for an assembly that, owing to its intended use, may require components that are disposed on a non-linear surface.

One such article of manufacture is an implantable medical device. These devices are implanted into a living being, human or species, to perform for diagnostic and or therapeutic reasons. One such device is an electrode array. This type of device includes some sort of carrier or frame on which plural exposed electrodes are mounted. Conductors, also part of the array, function as the array components over which currents are sourced to or sunk from the individual electrodes. Some electrode arrays are further constructed so that the actual components from which current is sourced to or sunk from the array are also mounted to the array. The array itself is designed for implantation against the tissue of a living being, including a human. More particularly, the array is positioned so that electrodes are able to flow current through tissue so that current flow will result in the desired physiological effect on the patient. Selective current flow through a patient is used for or has been proposed for the following therapeutic reasons: correcting cardiac arrhythmia; pain management; appetite suppression; control of incontinence; and the overriding of damaged neurological connections that have resulted in loss of muscle control and/or loss of feeling. Still another application of these arrays is to monitor the electrical impulses generated by the individual's neurological system. The electrodes of the array transmit signals representative of these electrical impulses to components off the array. The off array components may be able to use these signals to control the devices to which they are connected. These devices include, but are not limited to, mechanically powered exoskeleton units that move the individual, robotic linkages and artificial speech generators.

The Applicant's Assignee's FOLDABLE, IMPLANTABLE ELECTRODE ARRAY ASSEMBLY AND TOOL FOR IMPLANTING SAME, PCT Pub. WO 2009/11942 A2, U.S. patent application Ser. No. 12/873,397, US Pat. Pub. No. US 2011/0077660 A1, its IMPLANTABLE ELECTRODE ARRAY ASSEMBLY INCLUDING A CARRIER FOR SUPPORTING THE ELECTRODES AND CONTROL MODULES FOR REGULATING OPERATION OF THE ELECTRODES EMBEDDED IN THE CARRIER AND METHOD OF MAKING SAME, PCT Pub. No. WO 2011/017426 A2, U.S. Pat. Pub. No. US 2012/0310316 A1, the contents of which are incorporated herein by reference, disclose versions of these electrode arrays. Generally, the electrode arrays of these publications include a frame, sometimes called a carrier, formed from an elastic material. Electrodes are disposed over these frames. The frames of these disclosures are formed from Nitinol, a nickel titanium alloy. Given the conductive nature of these frames, it is necessary to form the electrodes themselves over electrically insulating layers. These documents state that it may be desirable to apply parylene-C to the elastic Nitinol carrier so that this material, once cured, functions as the insulating support layer. These documents actually state that it may be desirable to apply plural layers of parylene. Each layer, once cured, functions as the layer upon which one or more conductive components are formed. For example, the cured parylene layers closest to the elastic carrier serve as support layers on which conductors are formed. The outer layers of the parylene serve two functions. First these layers serve as the electrically insulating skin of the array. Secondly, at least one of these parylene layers typically also functions as the support layer over which the array electrodes are formed.

Parylene is a good electrical insulator, bonds well to superelastic material like Nitinol, is flexible once cured and accepts metal layers that are selectively etched to form conductors and electrodes. These are desirable qualities for an insulating layer that is part of an implantable electrode array. However, parylene has been found to have a characteristic that limits its suitable as an insulating layer for an implantable electrode array. Specifically, parylene absorbs relatively high quantities of water. An electrode array implanted into living tissue is surrounded by body fluids. These fluids are primarily water. Given the parylene tends to absorb water, there is a concern that, over time, a significant quantity of these bodily fluids could be absorbed into the parylene layers of the electrode array. This fluid, once absorbed into the parylene, can force the insulating layer to delaminate from the layers to which it is bonded. This delamination of the insulating layer can, in turn, result in the breakage and subsequent malfunctioning of the array itself.

Accordingly, there is an increasing interest in forming the insulating layers out of polymer other than parylene. One alternative polymer that can be employed in an electrode array as an electrically insulating layer is a liquid crystal polymer. This polymer, like parylene, has good bonding properties, is flexible when bonded, and accepts metal layers. In comparison to parylene, a liquid crystal polymer absorbs appreciably less water. Once implanted in a living being, the LCP insulating layer or layers of an electrode array absorb nominal amounts of body liquid and, by extension, are less prone to delaminate.

The Assignee's incorporated by reference PCT Pub. No. WO 2011/017426 A2, discloses that an electrode array with LCP insulating layers can be formed by first mounting some components to the array frame. Then the polymer, in the liquid state, is applied to the partially assembled array and allowed to cure. This method of assembly has been found to be expensive. Accordingly, there is an interest in forming implantable electrode arrays with liquid crystal polymer layers wherein the LCP itself is already in sheet form.

However, to date, it has proven difficult to manufacture electrode arrays with LCP that is already in the form of a cured sheet. This is because the sheets when applied to the frame or other layer over which it is bonded often seats unevenly over the underlying surface. This makes it difficult, if not impossible, to then apply the metal layers on the LCP insulation layer in a manner that ensures that conductive layers and/or electrodes remain bonded to the insulating layer.

SUMMARY OF THE INVENTION

This invention relates to a new and useful method of fabricating an implantable medical device that includes one or more layers support layers that is a thin, biocompatible polymer film. The method may be used to construct a device intended to provide a therapeutic effect and/or provide diagnostic information. Using this method, the device can be manufactured that has a substrate, intermediate layer, superstrate or other support layer formed of polymer that has a thickness of 1 mm or less.

One such device that can be fabricated according to the method of this invention is an electrode array designed for implantation into living tissue.

According to the method of this invention, the thin polymer film on which components are to be fabricated is initially applied to a backing. To perform this process, an adhesive is initially disposed on the surface of the backing on which the polymer film is to be bound. A piece of polymer film, 64 sometimes referred to as coupon, is applied to the backing. Once the coupon is applied to the backing, pressure is applied to the coupon while the assembly is at a temperature above ambient temperature and a pressure below ambient pressure. The pressure ensures the bonding of the film to the adhesive coating on the backing. Further, the pressure ensures that that film is at a relatively constant height above the backing.

The components that provided the intended therapeutic effect and/or diagnostic are the attached to the coupon. In some but not all versions of the invention, this attachment process includes the selective etching away of sections of the coupon. If the components are conductive, they can be attached to the coupon by selectively applying layers of metal to the exposed face of the coupon. This metal can be applied to form conductors. If the assembly under formation is an electrode array, spaced apart sections of metal are applied to the coupon to for the array electrodes. During the application of metal to the coupon, metal is sometimes deposited into the previously formed through openings in the coupon. The metal in these openings later function as vias through the insulating layers formed by the coupons.

Other components that form part of the completed device assembly may also be bonded to the exposed face of the polymer. These components include electrical components such as integrated circuits. Support members can also be mounted to the coupon. These support members include structural components that provide the coupon with at least some rigidity. These support members include materials that may be plastically deformable such as plastic or metal frames. Alternatively, these support materials may be formed from material that has some elasticity, such as frame members formed from Nitinol.

The piece of the polymer film is shaped to define a section of the film that is the support layer for the device under assembly. This process may be performed mechanically or electrically. Often, but not always, this process occurs before the below described removal, lift off, of the device from the backing.

In some constructions of the invention, one coupon to which components have been added may then be bonded to a second coupon. This process is performed by inverting one of the backed coupons so the exposed face of the coupon is directed to the exposed face of the second backed coupon. The coupons are then placed together and bonded by thermal compression bonding. Following the bonding of the coupons, the backing is released from one of the coupons. A new backed LCP layer may be bonded to this newly exposed face of the partially completed assembly.

As a consequence of the above processes, the work piece under assembly consists of plural LCP coupons that are bonded together. Conductors, other electrical components and structural members are sandwiched between these layers.

Once the multi-layer assembly is formed, some components may be attached to the exposed face of the outermost LCP coupon. The bottommost coupon is then released from the associated backing. Either before or after this process, the portions of the coupons that do not form the assembly are separated from the layers forming the assembly.

This invention provides a means to form components on cured sections of thin film polymer such as liquid crystal polymer films. During this process of this invention, the film is held to the backing such that the film has a substantially uniform height above the backing. Consequently, the surface of the polymer coupon is essentially planar and free from folds and bumps. This increases the likelihood that the assembly, collectively the polymer coupon and the components applied to it, will be structurally sound. Further, this invention provides a means to bond two polymer layers together. By extension, this invention provides a means to fabricate assemblies formed from three or more layers of thin polymer film. Components for obtaining diagnostic information or providing a therapeutic effect may be bonded to one or more of the plural layers of this multi-layer assembly.

Still another feature of this invention is that it is possible to simultaneously shape and process separate sections of a single backed polymer coupon. Each coupon section can be shaped to have the features that will be found in a separate assembly. Electrical components and structural components can be applied to or placed on the individual sections of the coupon. The different sections of each coupon can be processed to form sections of separate assemblies under construction. Thus, this invention facilitates the batch processing of a thin polymer film so that the separate sections of the coupon form the layers of separate finished assemblies.

In this method assembly is the coupon is removed from the backing by dissolving the adhesive holding the coupon to the backing. Once the adhesive is dissolved, the polymer and attached components are subjected to essentially no mechanical stress when lifted away from the backing. The essential elimination of this stress results in a like elimination that this stress could damage either the damage to the polymer support layer or the component(s) attached to the layer.

The processes of this method can be practiced together. Alternatively, it is a feature of this invention that the processes of this method can, is appropriate, be practiced independently from each other.

BRIEF DESCRIPTION OF THE DRAWINGS

The invention is pointed out with particularity in the claims. The above and further features and advantages of the invention are understood from the following Detailed Description taken in conjunction with the following drawings in which:

FIG. 5 is a cross sectional view along line 5-5 of FIG. 4 showing a portion of the frame coupon after there has been an application of an oxidation layer over selected surfaces of the frame coupon;

FIG. 6 is a side diagrammatic illustration of the placement of a LCP coupon backing on a vacuum chuck;

FIG. 7 is a side diagrammatic illustration of the coating of adhesive over the LCP coupon backing of FIG. 7;

FIG. 19 is a cross sectional view of the LCP coupon of FIG. 17 after through openings have been formed in the coupon;

FIG. 20 is a cross sectional view of the LCP coupon of FIG. 19 after metal has been deposited in some of the openings to form core cores that extend through the coupon;

FIGS. 30, 31 and 32 are a sequence of cross sectional views depicting the shaping of the LCP coupon on which plural array third intermediate LCP layers are fabricated;

DETAILED DESCRIPTION

I. An Electrode Array that can be Assembled According to this Invention

Figure 1:
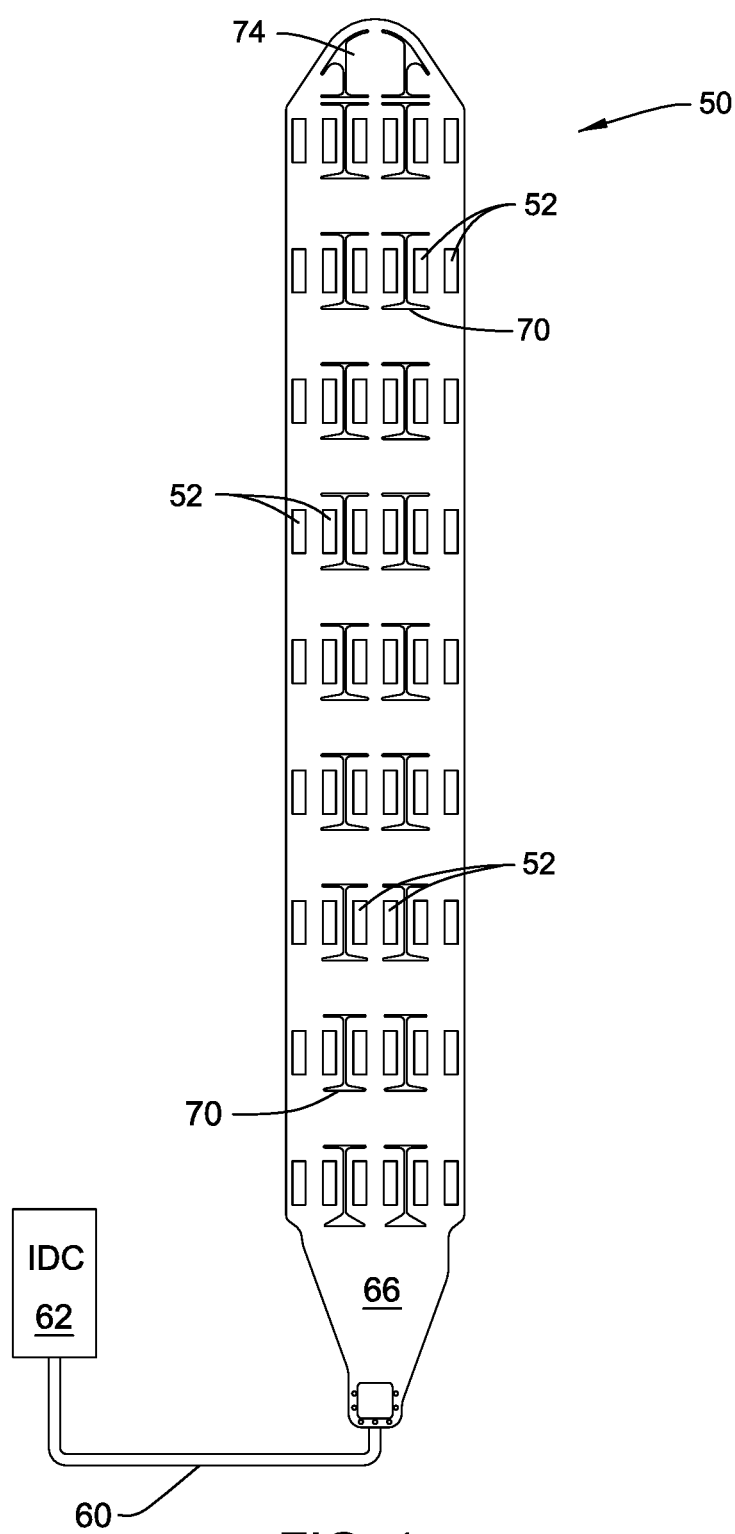
FIG. 1 illustrates an electrode array that is at least partially fabricated according to the method of this invention.
Figure 1A:
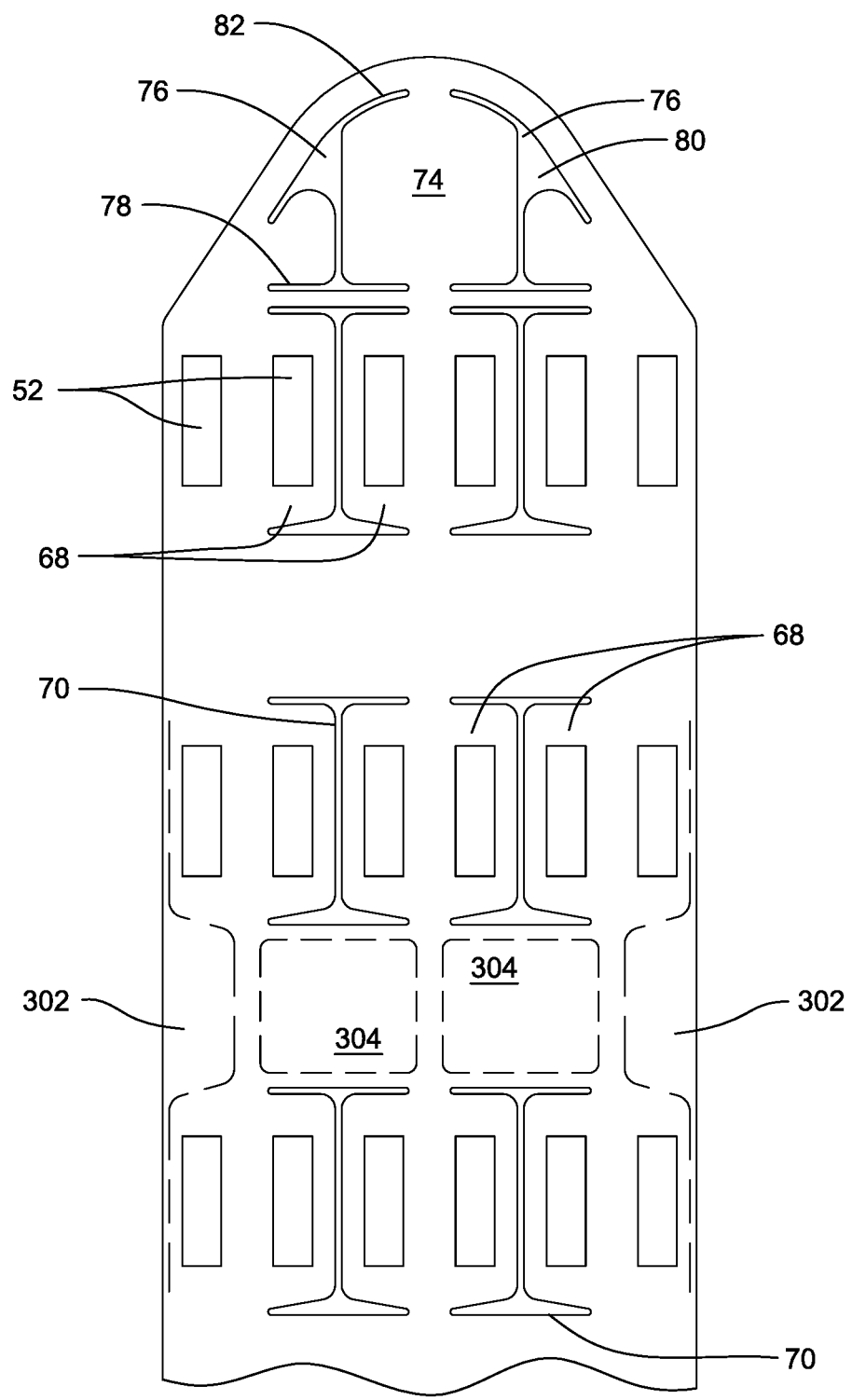
FIG. 1A is an enlarged view of the distal end of the electrode array of FIG. 1.
Figure 2:
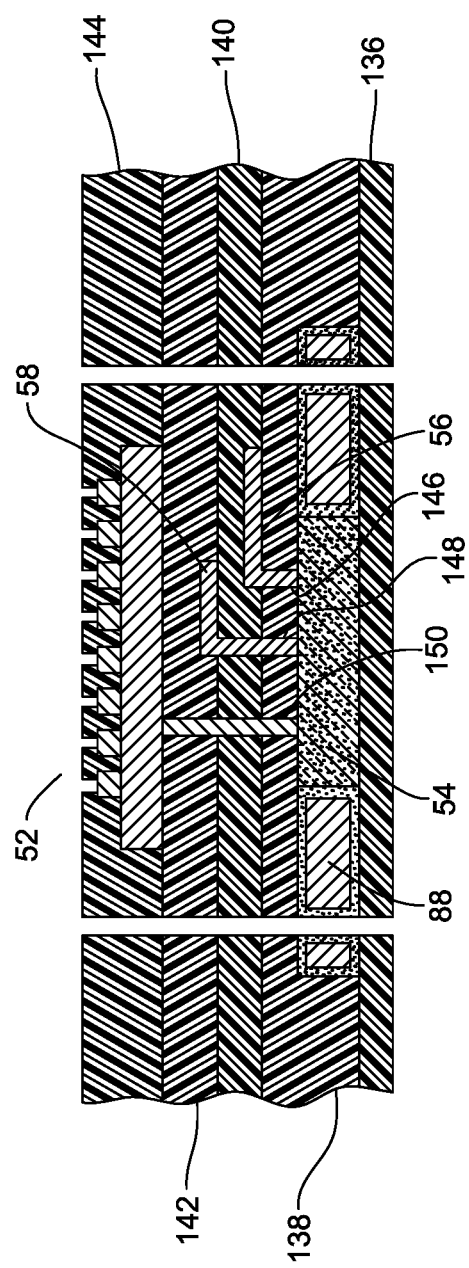
FIG. 2 is a cross section view of the electrode array of FIG. 1.

FIGS. 1, 1A and 2 illustrate an implantable medical device 50 constructed according to the method of this invention. This device 50 is an electrode array and is referred to as such throughout the remainder this document. Electrode array 50 includes a number of spaced apart electrodes 52. In the illustrated version of the invention, the electrodes 52 are arranged in a row by column pattern. Many electrode arrays 50 constructed using the method of this invention have at least 10 electrodes. Still other electrode arrays constructed according to this invention have 20 and even 40 or more electrodes. In the depicted version of the invention, each electrode is rectangularly shaped. The size and shape of the electrodes 52 can vary with the function of the array 50. Thus it should be understood that in some versions of the invention, each electrode may have a width of 10 mm or less, 5 mm or less or in some applications, 2 mm or less. The length of an individual electrode 52 may be 40 mm or less, 20 mm or less, 10 mm and less and even 5 mm or less.

Array 50 also includes a number of control modules 54, one seen in FIG. 2. Each control module 54 is connected to one or more electrodes 52. Each control module 54 is an application specific integrated circuit (ASIC). The circuit includes components able to source current from/sink current to the associated electrodes 52. In FIG. 2, the control module 54 is shown disposed below the electrode 52 with which the module is associated.

Conductors 56 and 58 (one of each shown) extend from the control modules 54. Conductors 56 and 58 are connected to a cable 60 that extends from the proximal end of the electrode array assembly 50. (Here "proximal" means toward the end of the array 50 at the bottom of FIG. 1. "Distal" means toward the end of the assembly at the top of FIG. 1.) Not illustrated are the individual conductors internal to cable 60. Cable 60 is connected to an implantable device controller (IDC) 62. The IDC 62 contains the power source for the currents that are flowed between the electrodes 42. IDC 62 also contains a controller that generates the instructions that indicate between which electrodes 52 the currents are to be flowed. The structure of the IDC 62 is not part of the present invention.

Electrode array assembly 50 is shaped to have a base 66 that is the most proximal portion of the assembly. Nine rows of electrodes 52 are located forward of base 66. Each row of electrodes 52 is longitudinally spaced from the adjacent row (or rows) of electrodes. This spacing is often between 0.5 and 10 mm. In the illustrated version of the invention, there are six electrodes 52 in each row of electrodes. The array 50 is constructed so that the inner four electrodes 52 in each row are each seated on a separate rectangularly shaped tab 68. Each electrode-carrying tab 68 is separated on three sides from the surrounding portions of the array 50. More particularly, interleaved with each row of electrodes 52 are two I-shaped slots 70. Each slot 70 thus defines the perimeters of two tabs 68. In some versions of the invention, slots 70 are shaped so that each tab 68 has a length (measurement along an axis parallel to the longitudinal axis of assembly 50) of between 0.5 to 5 mm. Often this length is between 2 and 4 mm. Each tab 68 has a width, (measurement along the axis perpendicular to the longitudinal axis of assembly 50 in the plane of FIG. 2) of 0.25 to 2 mm. In many versions of the invention, this width is between 0.5 to 1 mm. The distance across each slot 70 is approximately 75 microns. Array 50 is thus formed to have two columns of I-shaped slots 70. Within each row of electrodes 52, the two slots 70 are spaced laterally apart from each other and are laterally aligned with each other.

Immediately forward of the distal most row of electrodes 52 array 50 is formed to have a head 74. Head 74 is the most distal portion of the array 50. The head 74 is shaped to have an arcuately shaped leading edge. The arc forming this leading edge is centered on the longitudinal axis that extends along the array. On each side of the front edge, the head 74 is shaped to have an edge that, is as it extends proximally away from the distal end, extends away from the array longitudinal axis.

Array head 74 is formed to have two slots 76. Slots 74 are located opposed sides and symmetric relative to the array longitudinal axis. Each slot 76 forms a number of sections. Specifically each slot 76 has a base section 78 that is parallel to and laterally offset from the array longitudinal axis. More particularly each slot base section 76 is in registration with a separate one of the rows of slots 70. The most forward portion of each slot section 76 opens into a primary opening 80. Each primary opening 80 is generally in the form of a triangle. The most acute apex of opening 80 is directed towards the most distal end of the head 74. Each slot 76 is further formed to have a distally directed extension 82. Each distal extension 82 extends forward from the apex of the slot primary opening 80. From the associated slot primary opening 80, each slot distal extension 82 curves both distally forward and towards the longitudinal center axis of the array 50. While the slot distal extensions 82 curve towards each other, the extensions do not connect.

Figure 4:
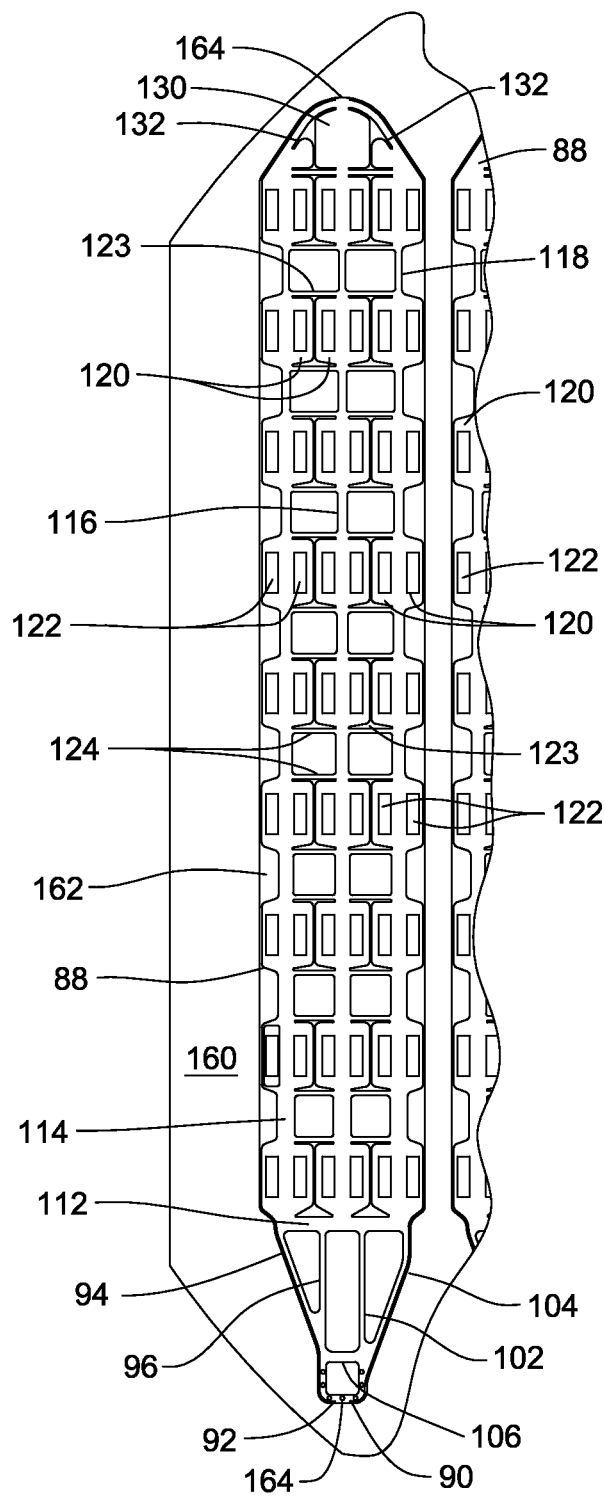
FIG. 4 is an enlarged view of a section of the frame coupon of FIG. 3.

As illustrated by FIG. 2, embedded in and part of the electrode array 50 is a frame 88. Frame 88 is formed from a superelastic material. Superelastic material is material that, after being subjected to the strain induced by appreciable rolling, folding or bending, returns to its initial shape. In one version of the invention, the frame 88 is formed from a nickel titanium alloy such as Nitinol. As seen best in FIG. 4, frame 88 is formed from a single piece of Nitinol and is shaped to have a proximal located tail 90. Frame 88 also has a head 130 that is spaced forward of tail 90. Three parallel spaced apart bridges 114, 116 and 118, extend from the frame tail 90 towards the frame head 130.

Frame tail 90 includes two beams 92 and 112 that extend perpendicularly to the longitudinal axis of the array 40. Beam 92, the more proximal of the two beams, is the shorter of the two beams. Beam 112, is longer than and is located distal to beam 92. Both beams 92 and 112 are centered on the longitudinal axis of the array 40. A number of additional beams are located between beams 92 and 112. Two beams 96 and 102 extend between beams 92 and 112. Beams 96 and 102 are perpendicular to beams 92 and 112 and extend along axes parallel to the longitudinal axis of frame 88. Another beam, beam 94 extends distally and outward from a side of beam 96 to the adjacent end of beam 112. A beam 104 extends outwardly and distally forward from a side of beam 102 to the adjacent end of beam 112. The location along beam 96 from which beam 94 extends distally forward is forward of the location along beam 102 from which beam 104 extends. A beam 106, that is parallel to beam 92, extends between beams 96 and 102. Beam 106 extends perpendicularly outwardly from beam 102 from approximately the location along beam 102 from which beam 104 extends distally forward.

Bridges 114, 116 and 118 extend distally forward from beam 112. Bridge 116 is centered along the longitudinal axis of the frame 88. Bridges 114 and 118 are spaced apart symmetrically relative to bridge 116. A number of three-sided tabs 120 extend outwardly from bridges 114, 116 and 118. Frame 88 is shaped so that tabs 120 have major axes that are parallel to the longitudinal axis of the frame. Tabs 120 are arranged in pairs; where a tab 120 extends outwardly from one side of a bridge 114, 116 or 118, a laterally aligned tab 120 extends outwardly from the opposed side of the same bridge. The tabs 120 are further so that, where the tabs extend outwardly from one bridge 114, 116 and 118, tabs also extend outwardly from the laterally adjacent sections of the other two bridges. Frame 88 is therefore constructed so that the tabs 120 are arranged in rows wherein, in the illustrated version of the invention, there are six tabs in each row. The rows of tabs 120 are longitudinally spaced apart from each other.

In some versions of the invention, frame 88 is shaped so that the tabs 120 have a length, distance along the axis parallel to the longitudinal axis of the frame 88, of between approximately 0.5 and 4.0 mm. The width of the tabs 120, the distance the tab extends away from the associated bridge 114, 116 or 118, of between approximately 0.5 and 2.0 mm. The frame 88 is formed so that each row of tabs 50 is spaced approximately 0.5 to 4.0 mm away from the row of laterally adjacent tabs. It should be further understood that frame 88 is further shaped so that each tab 120 that extends outwardly from center located bridge 116 is spaced away from the adjacent tab that extends outwardly from the adjacent bridge 114 or 118. This separation is typically a minimum of 100 microns.

Frame 88 is further formed so that each tab 120 is shaped to have a center located rectangular opening 122. The major axes of the tab openings 122 are, centered on the major axes of the tabs 120. Each opening 122 is dimensioned to receive an individual control module 54. Also the outermost tabs 120, the tabs that extend outwardly from the outer side edges of bridges 114 and 118, have tapered front and rear sections, the sections perpendicular to the longitudinal axis of the frame. These sections (not identified) are tapered so that that length of the tab 120 decreases slightly as the tab extends away from the bridge 114 or 118 with which the tab is integral. The outer corners of the tabs (corners not identified) are rounded.

A number of rectangularly shaped beams 124, also part of frame 88, connect bridges 114, 116 and 118 together. The frame 88 is shaped so that, where a beam 124 extends between bridge 114 and bridge 116, a laterally adjacent beam 124 extends between bridge 116 and bridge 118. The beams 124 are arranged so that a pair of laterally adjacent beams is located immediately in front of and rearward of all but the most proximal row of tabs 120. A pair of beams 124 are located immediately forward of the most proximal row of tabs 120. In the illustrated version of the invention, there are nine rows of tabs; accordingly there are 18 pairs of laterally adjacent beams. Each beam 124 has a width, the distance parallel to the longitudinal axis of the frame 88, which is typically 2.0 mm or less, and often 0.5 mm or less.

As described above, the tabs 120 that extend outwardly from bridge 116 are spaced away from the adjacent tabs 120 integral with bridges 114 and 118. The tabs 120 are spaced longitudinally away from the adjacent inter bridge beams 124. Thus, between bridges 114 and 116 and between bridges 116 and 118 there are I-shaped slots 123 around the tabs 120. As discussed below the void of each slot 123 is the primary void of a separate one of the array slots 70. Thus, each frame slot 123 has shape substantially identical to an array slot 70. Each frame slot 123 has a width that is approximately 25 microns wider than an array slot 70.

Frame head 130 is formed to have two slots, slots 132. The void of each slot 132 is the primary void of a separate one of the array slots 76. Accordingly, each slot 132 has a shape that corresponds to the shape of the corresponding arrays slot 76.

Returning to FIG. 2 it can be seen that layers of liquid crystal polymer (LCP) insulating material are disposed around the opposed surfaces of frame 88. One layer of LCP, LCP layer 136, is disposed over the passive side of the frame 88 and the control modules 54 encased in the frame. (The "passive" side of the array/frame is the side opposite the side on which the electrodes 52 are disposed. The "active" side of the array/frame is the side on which the electrodes 52 are disposed.) The outer surface of LCP layer 136 thus functions as the passive side face of the array 50. A first intermediate LCP layer, LCP layer 138, is disposed over the active side of frame 88 and embedded control modules 54. Where the passive side surface of LCP layer 138 is not disposed against the control modules 54 or frame 88 this surface is disposed over layer 136. A second intermediate LCP layer, layer 140, is disposed over the active side surface of first intermediate LCP layer 138. A third intermediate LCP layer, layer 142, is disposed over the active side surface of second intermediate LCP layer 140. An active side LCP layer, layer 144, is disposed of the active side surface of third intermediate LCP layer 142. The outer surface of LCP layer 144 functions as the active side exposed face of the array 50.

The electrodes 52 are embedded in the active side LCP layer 144. One layer of conductors, specifically conductors 56, are embedded in the second intermediate LCP layer 140. A second layer of conductors, specifically conductors 58, are embedded in the third intermediate LCP layer, 142. Vias 146 are formed in and extend through LCP intermediate layer 138 between the control modules 54 and conductors 56. Vias 148 are formed in and extend through LCP intermediate layers 138 and 140 between control modules 54 and conductors 58. Vias 146 and 148 thus provide the electrical connections between the control module 54 and, respectively, conductors 56 and 58. Plural vias 150 are formed in and extend through intermediate LCP layers 138, 140 and 142. Each via 150 provides an electrical connection from the control module 54 to the electrode 52 with which the module is associated.

II. Method of Assembly

Figure 3:
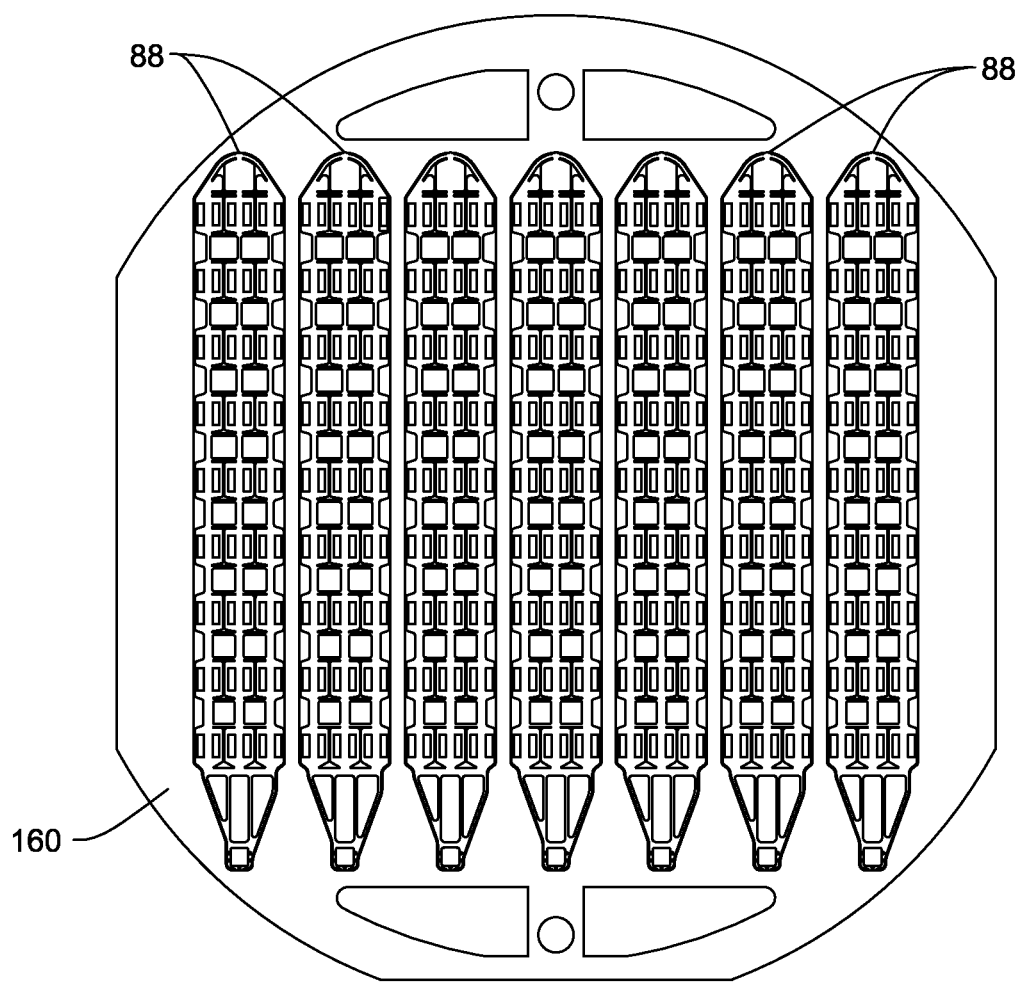
FIG. 3 is a plan view of a coupon of this invention on which a number of array frames are formed.

The assembly of the electrode array 50, actually the batch assembly of plural arrays 50, starts with the fabrication of plural frames 88. Frames 88 are fabricated by shaping a sheet section of the material from which the frames are formed. This sheet is known as a coupon 160, seen in FIG. 3. In the described version of the invention coupon 160 is formed from Nitinol and has a thickness between 25 and 100 microns. More specifically, frame coupon 160 has a thickness that is approximately 10 microns greater than the height of the control modules 54 disposed in the frames 88.

Using a chemical etch processes, portions of the coupon 160 are removed to define a number of through openings. Prior to the etching of the coupon, the coupon sections that are to remain parts of the frame are masked to prevent their removal. The openings in the coupon 160 defined in this etching process include through openings that define both the outer perimeter of plural frames 88 as well as the structural features of each frame. The perimeter the outer shape of an individual frame is defined by a slot 162 seen in FIG. 4. The width of the slot 162 varies along the perimeter of the associate frame 88 so as to define the outer shape of the frame. For example, where a tab 120 extends outwardly from one of the bridges 114 or 118, slot 162 is of narrow width. Adjacent the tab-free portions of bridges 114 and 118, slot 162 has a wider width.

In this etching step, each slot 162 is formed so as to not completely sever the frame 88 defined by the slot from the surrounding portion of the coupon. Instead the slot 162 is broken into sections by a number of retaining tabs 164. Each tab 164 (one seen in FIG. 4A) extends between the frame 88 with which the tab is integral and a section of the coupon 160 that surrounds the frame. While only one tab 164 is seen in FIG. 4A, typically plural tabs 164 extend between each frame 88 and the rest of the coupon 160. In the described version of the invention there are two tabs 164. The tabs 164 are centered on opposed of the longitudinal center axis of the frame 88 with which the tabs are associated.

In some versions of the invention, plural etching or other material removal processes are performed on the coupon 160 in order to define the frames 88. One reason to perform the plural etching processes is to shape the coupon 160 so that the tabs 164 have thickness less than the thickness of the portions of the coupon 160 that have not been removed. In some versions of the invention, these plural etching processes are performed so that the tabs 164 have thicknesses that are approximately 30 to 70% of the thickness of the unetched coupon sections.

After the Nitinol coupon 160 is shaped, oxide is deposited on the portions of the coupon that form the frames 88. This process is performed by first masking off the portions of the coupon 160 that will not function as array frames 88. This mask is often a photo-resist resin. After the masking, the coupon is placed in a chamber and silicon oxide is deposited on the unmasked portion of the coupon. The oxide is deposited by a plasma enhanced chemical vapor deposition process. The silicon oxide coats the unmasked portions of the coupon as seen in FIG. 5. The silicon oxide coating, called out as layer 163 in FIGS. 5 and 15, has a thickness of approximately 1000 to 10,000 Angstroms. In some versions of the invention the coating is more often between 1,500 and 4000 Angstroms.

After the coupon 160 is shaped to define the frames 88, the coupon may be further shaped to bend the frames. This processing is performed if the array 50 is designed for application over tissue that is not planar. In this instance, the frames, while still part of coupon 160, are permanently bent so as to approximate the shape of the surface of the tissue to which the assembly arrays 50 are applied. For example, if arrays 50 are intended for application over the spinal cord, each frame 88 is shaped so that, on each side of its longitudinal axis, the frame curves out of the plane of the coupon 160. Not illustrated is a depiction of the frames 88 extending out of the plane of the coupon 160.

Frame shaping may be performed by pressing the coupon 160 between opposed dies. Each die has geometric features that bend the attached frames 88 into the desired shape. Once the frames 88 are so pressed, heat is applied to set the frames 88. The heat may be sourced from heaters in the individual dies, external heaters or heat transferred from liquid surrounding the dies. As a consequence of the simultaneous bending and heating of the frame 88, the carriers develop the desired curved shape, undergo the desired plastic deformation.

Figure 8:
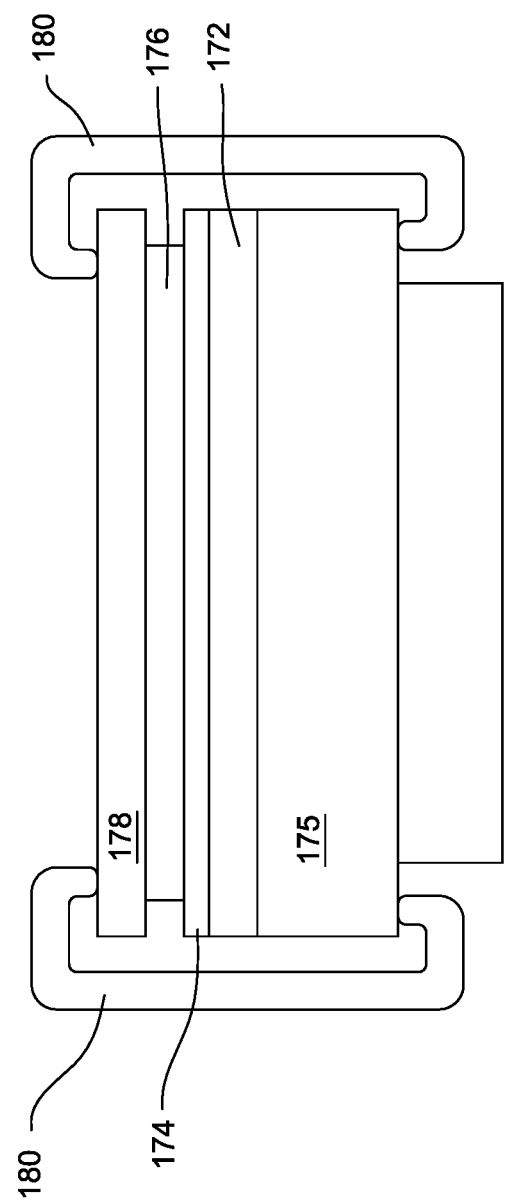
FIG. 8 is the side diagrammatic depiction of the placement of the LCP coupon and glass plate over the LCP coupon backing and the clamping of the coupon and glass plate to the press chuck

An LCP coupon, coupon 176, first seen in FIG. 8, is shaped to define the plural passive side LCP layers 136 to which the frames 88 are bonded. As depicted by FIG. 6, this process starts with the placement of a backing 172 on a vacuum chuck 170. A vacuum chuck is a chuck to which an object such as the wafer can be held using a suction drawn and that can spin. This particular vacuum chuck 170 is, as discussed below, rotated at speeds up to 10,000 RPM. Backing 172 is formed from a rigid material able to withstand the below described processing steps without fracturing. In one version of this invention backing 172 is silicon wafer generally in the shape of a circle with a slice section at one end removed. The backing 172 may have a diameter of 150 mm and a thickness of 500 microns.

Once backing 172 is disposed on chuck 170, an adhesive 174 is evenly applied to the exposed face of the backing, as represented by FIG. 7. One such adhesive that is applied to backing 172 is a formed from a blend of phthalic anhydride and ethanediol sold under the trade mark CRYSTALBOND by electron Microscopy Services of Hatfield, Pa., US. To ensure that the adhesive 176 is evenly applied to the backing 172, once the adhesive is applied to the backing, chuck 170 is rotated. Specifically, chuck 170 is initially rotated at a speed of approximately 500 RPM for approximately 10 seconds. This rotation of chuck 170 and, by extension backing 172 and adhesive 174, roughly spreads the adhesive over the whole of the backing. Chuck 170 is that rotated at a speed of between 1,000 to 3,000 RPM for approximately 5 to 20 seconds. This rotation of the backing 172 and the adhesive 174 evenly spreads the adhesive over the whole of the backing. These spin steps are performed at room temperature. At the end of these steps, the exposed face of backing 172 is coated with a layer of adhesive 174 that is approximately 1 to 5 microns thick. The adhesive 174 is disposed over the backing 172 so that there is a variation in its thickness of less than 1%.

After adhesive 174 is evenly spread over backing 172, the backing is seated on a press chuck 175 represented in FIG. 8 by a block.

Figure 9:
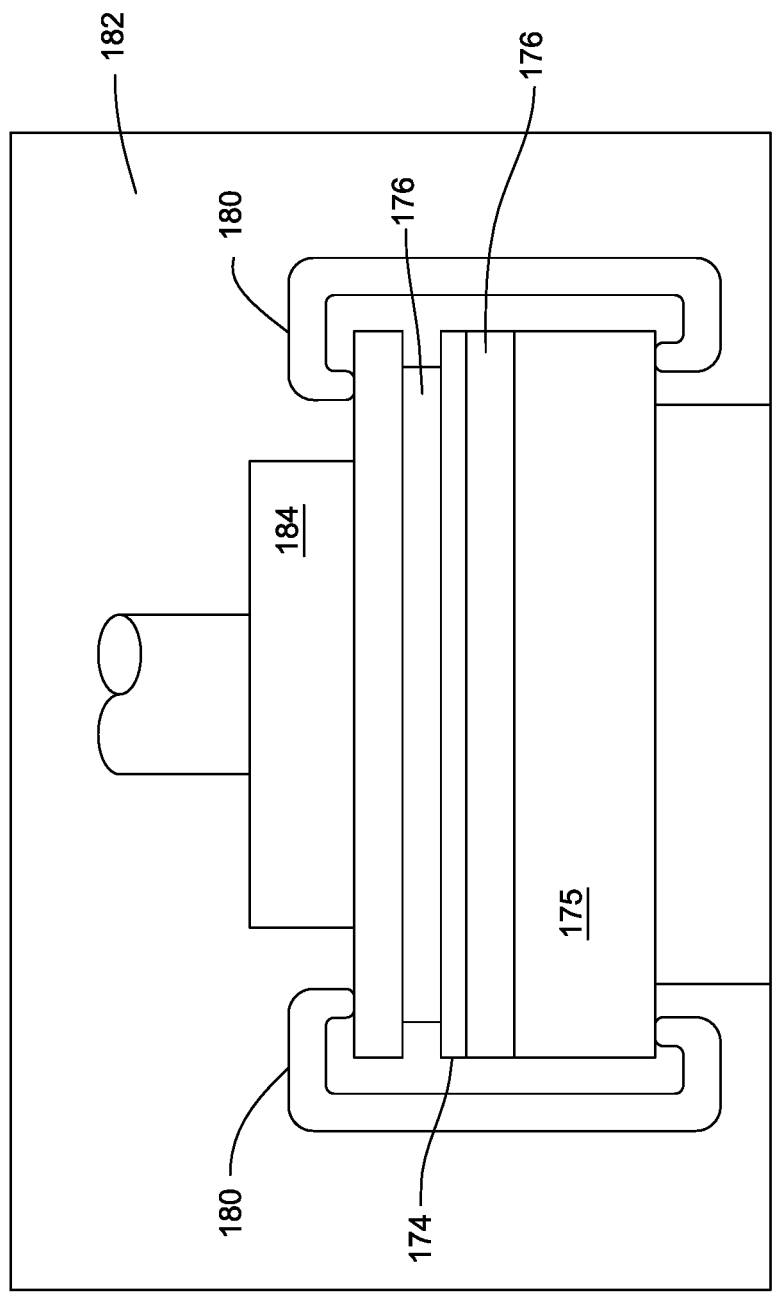
FIG. 9 is a side diagrammatic depiction of the pressing of the LCP coupon to the backing.

After the backing 172 is transferred to the press, adhesive 174 is applied to backing 172, the LCP coupon 176 is applied to the exposed surface of the adhesive as represented by FIG. 8. The coupon 176 has a thickness of 50 microns. LCP coupon 176 has a shape that approximates the shape of backing 172. Coupon 176 has a surface area that is greater than the surface area of the support layers, layers 136 that the coupon is shaped to form. Coupon also has a surface area that is less than the surface area of the backing 172. Specifically, LCP coupon 176 is shaped so that when the coupon is applied to the adhesive 174, the outer perimeter of the coupon is recessed approximately 5 to 50 microns inwardly from the outer perimeter of backing 172. For purposes of illustration, this difference in surface areas is exaggerated in the drawings As also represented by FIG. 8, a glass plate 178 is disposed over the LCP coupon 176. Plate 178 has a thickness of between 0.5 to 3.0 cm. Glass plate 178 has a surface area such that the plate extends beyond the outer perimeter of both backing 172 and coupon 178. More particularly, while not seen in FIGS. 8 and 9, plate 178 extends at least 0.5 cm beyond the perimeter of backing 172. Clamps 180, (two shown), extend from the exposed surface of the glass coupon to press chuck 175. Clamps 180 thus hold glass plate 178 both to press chuck 175 and over LCP coupon 176. The clamped assembly is then transferred to a bond chamber 182, the pressure of which can be controlled. In FIG. 9, bond chamber 182 is represented by the background rectangle.

Figure 10:
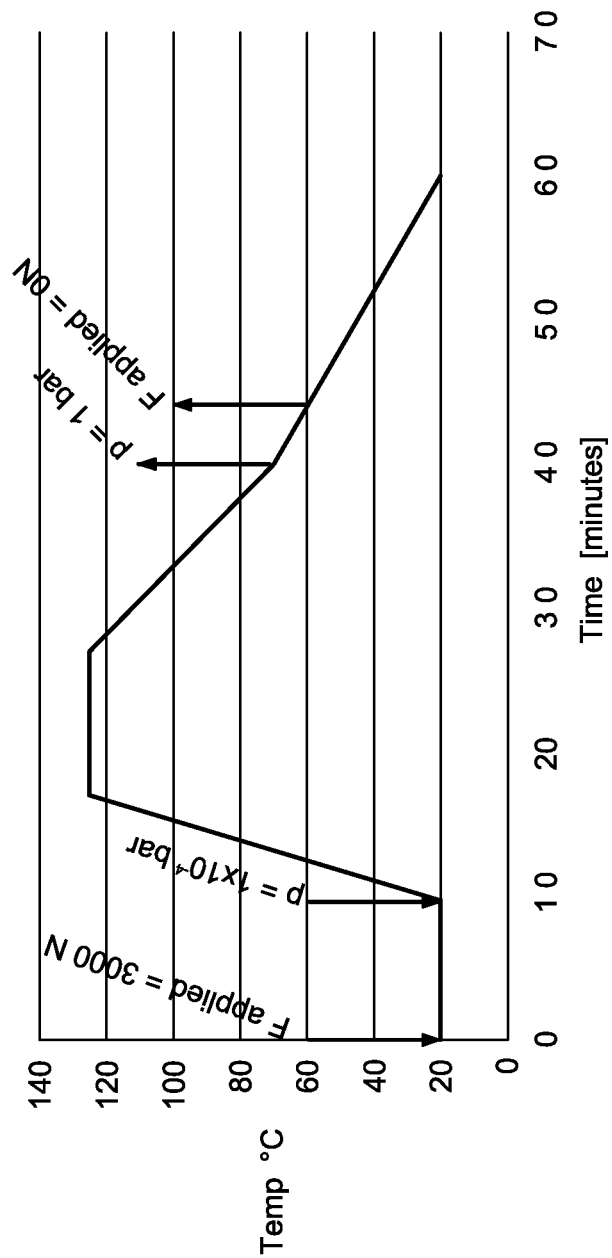
FIG. 10 is a time line representation of the steps of the pressing process executed to bond an LCP coupon to the back.

Once the clamped assembly is positioned within the bond chamber 182, a piston head 184, seen in FIG. 9, is pressed against the exposed face of the glass plate 178. Piston head 184 is urged against glass plate so as to apply a force of approximately 3000 Newtons. As represented by FIG. 10, almost immediately after the forcing of piston head 184 against plate 178, a suction is drawn on chamber 182 to lower the pressure. In one version of this invention, the pressure in chamber 182 is lowered to $10^{-4}$ bar. It takes approximately 10 minutes to lower chamber pressure to this pressure. During these steps, chamber temperature is maintained at ambient levels, represented in FIG. 10 by 20° C.

Once the pressure in chamber 182 falls to the target level, the temperature in the chamber is raised while maintaining the pressure on plate 178. In one version of this invention, chamber temperature is raised to approximately 125° C. It takes approximately 5 to 10 minutes for the chamber temperature to rise to this level. Once the chamber temperature reaches the target level, chamber temperature and pressure are maintained while maintaining the press force on the plate 178 and the underlying LCP coupon 176. In some versions of the invention, the assembly is maintained at this state for a period ranging between 10 and 30 minutes. After this period of maintaining constant temperature and pressure, the temperature is allowed to drop towards back to ambient levels. After approximately 10 to 20 minutes, the temperatures will have dropped to 70° C. Once the temperature has fallen to this level, pressure in vacuum chamber 182 is allowed to rise to ambient levels. Once the pressure in chamber 182 rises to ambient level, press head 182 is retracted away from plate 178 a sufficient distance to allow the clamped assembly to be removed from vacuum chamber 182, (step not shown).

Figure 11:
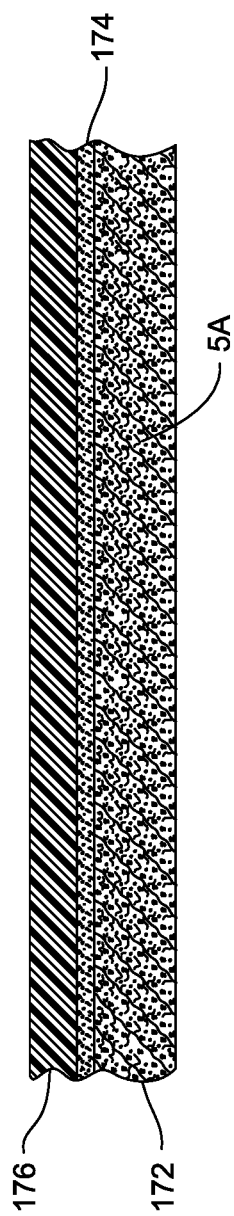
FIG. 11 is a cross sectional view of the LCP coupon bonded to the backing.

Clamps 180 are removed. Glass plate 178 is lifted off the LCP coupon 176. The backing-adhesive-LCP coupon assembly is lifted of press chuck 175. (Steps not illustrated). At this time, as represented by FIG. 11, the LCP coupon 176 is firmly attached to the backing 172 by adhesive 174 as represented by FIG. 11. As a result of the pressing under vacuum and heat process, the outer surface of the coupon 176 is of uniform height over the backing 172. Here "uniform height" is understood that the height of the surface of the LCP coupon 176 above backing 172 varies by less than 5% and more preferably 1.5% or less.

Figure 12:
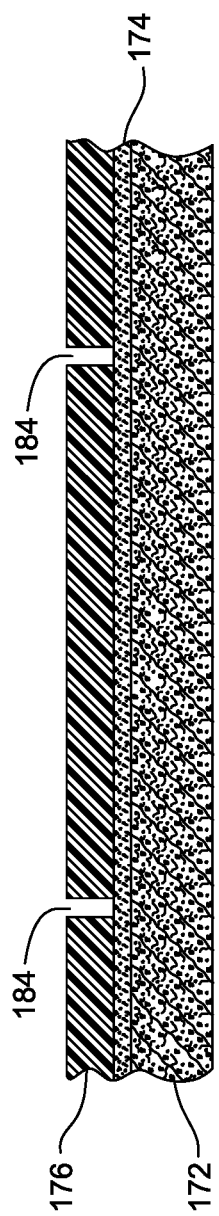
FIG. 12 is a side cross sectional view of a section the LCP coupon of FIG. 11 after the coupon has been shaped to form an electrode array passive side layer.

LCP coupon 176 is now ready for addition processing so that one series of steps, the coupon can be shaped to form plural array passive side LCP layers 136. In this process, portions of the coupon 176 are selectively removed. This process is performed by first applying a photo resist over the portions of the coupon 176 through which slots are not to be formed. Then, in an oxygen plasma reactive ion etching (O2 Plasma RIE) process, the unmasked portions of the LCP coupon are removed. The mask material is then removed from the remaining sections of the coupon 176. The above steps are performed while the coupon 176 remains bonded to backing 172. As a result of these processes coupon 176 now appears as depicted in FIG. 12. In this Figure LCP coupon is substantially as it appeared in FIG. 11. Now though, as seen in FIG. 12, a number of slots, two slots 184 and 186 shown, extend through the coupon 176. As will be clear from the following description and subsequent drawings, each of the slots formed in LCP coupon 176 become a section of one of the slots 70 and 76 that extend through the array 50. Slots 184 and 186, for example, are sections of the top and bottom sections of one of the tab 68-defining slots 70. In other words it will be seen that, as the array 50 is built, one of the ASIC-embedded and electrode carrying tabs will be built up between slots 184 and 186.

In the next series of steps, the frame coupon 160 is bonded to the exposed face of the LCP coupon 176. To prepare the LCP coupon 176 for the actual bonding, this surface is exposed to oxygen plasma. This exposure in a vacuum chamber. This exposure to the oxygen plasma roughens the surface of the LCP coupon. This exposure is for a period approximately 20 minutes.

Figure 13:
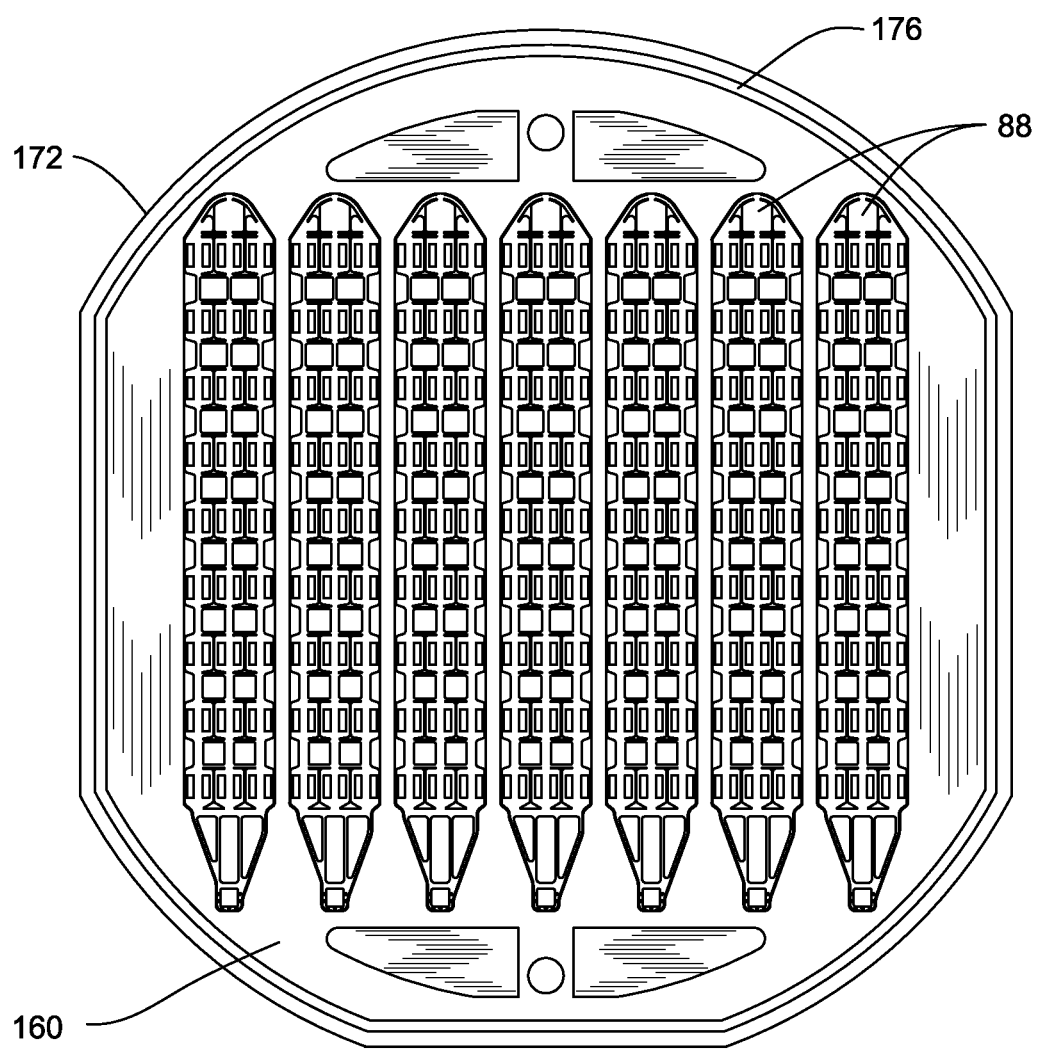
FIG. 13 is a plan view of the frame coupon disposed over the LCP coupon on which the electrode array passive side layers are formed.
Figure 15:
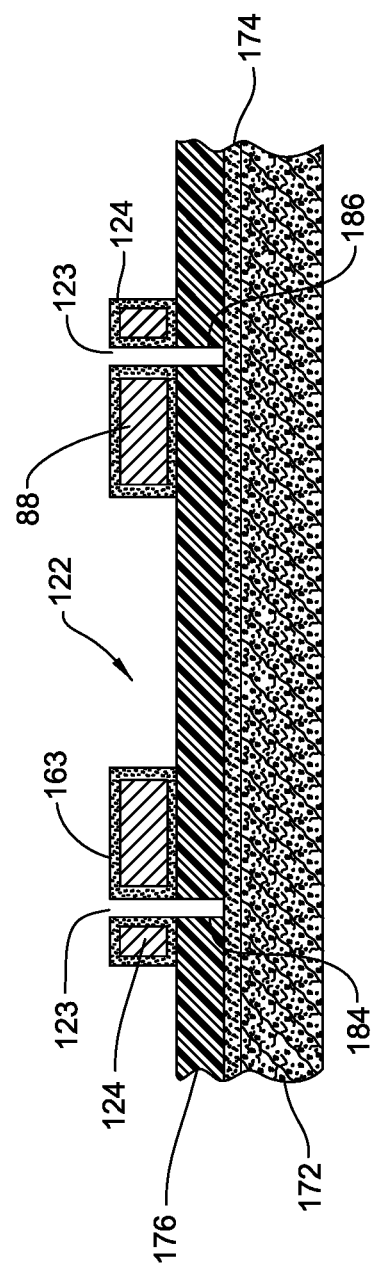
FIG. 15 is a cross sectional view of a portion of a frame mounted to the LCP coupon on which the electrode array passive side layers are formed.

Once the surface of the LCP coupon 176 is so roughened, frame coupon 160 is positioned over the LCP coupon 176. Specifically the frame coupon 160 is so positioned so that the frame coupon slots 123 and 132 are in registration over the complementary slots formed in the LCP coupon 176. This is seen in FIG. 15, wherein the opposed parallel sections of one the frame coupon I-slots 123 is in registration over the LCP coupon slots 184 and 186. In FIG. 13, the extent to which the outer perimeter of LCP coupon 176 is inwardly recessed from back 172 and the extent to which the outer perimeter of the frame coupon 160 is inwardly recessed from the outer perimeter of the LCP coupon are exaggerated for purposes of illustration.

To perform the actual frames to LCP coupon bonding, the multi-layer assembly is placed in a vacuum pressure chamber. A piston is disposed against the Nitinol coupon while under a vacuum of approximately 0.1 mBar. The piston force is between 500 and 3000 Newtons and typically between 700 and 1500 Newtons. The chamber is heated to a temperature between 200 and 300° C. This is the temperature range at which the surface of LCP coupon 176 becomes semi-liquid. Under these conditions, the semi-liquid LCP of coupon 176 embeds into the silicon oxide roughed portions of the frame coupon 160. Thus, upon completion of this process, the silicon oxide roughed portions of the frame coupon 160 are interlocked with, bonded to, the underlying sections of the LCP coupon. The oxide-free portions of the Nitinol coupon 160 are smoother than then the oxide coated portions of the coupon 160. Consequently during this thermal compression bonding process, the LCP of the coupon 176 do not interlock or bond with these oxide-free sections of sections of frame coupon 160.

Once the frames 88 are bonded to LCP coupon 176, the sections of the frame coupon 160 not part of the frames is lifted off the LCP coupon 176. This process is performed first mechanically serving the tabs 164 (FIG. 4) from the frames 88. The remnants of coupon 160 are manually lifted off the LCP coupon 176.

Figure 14:
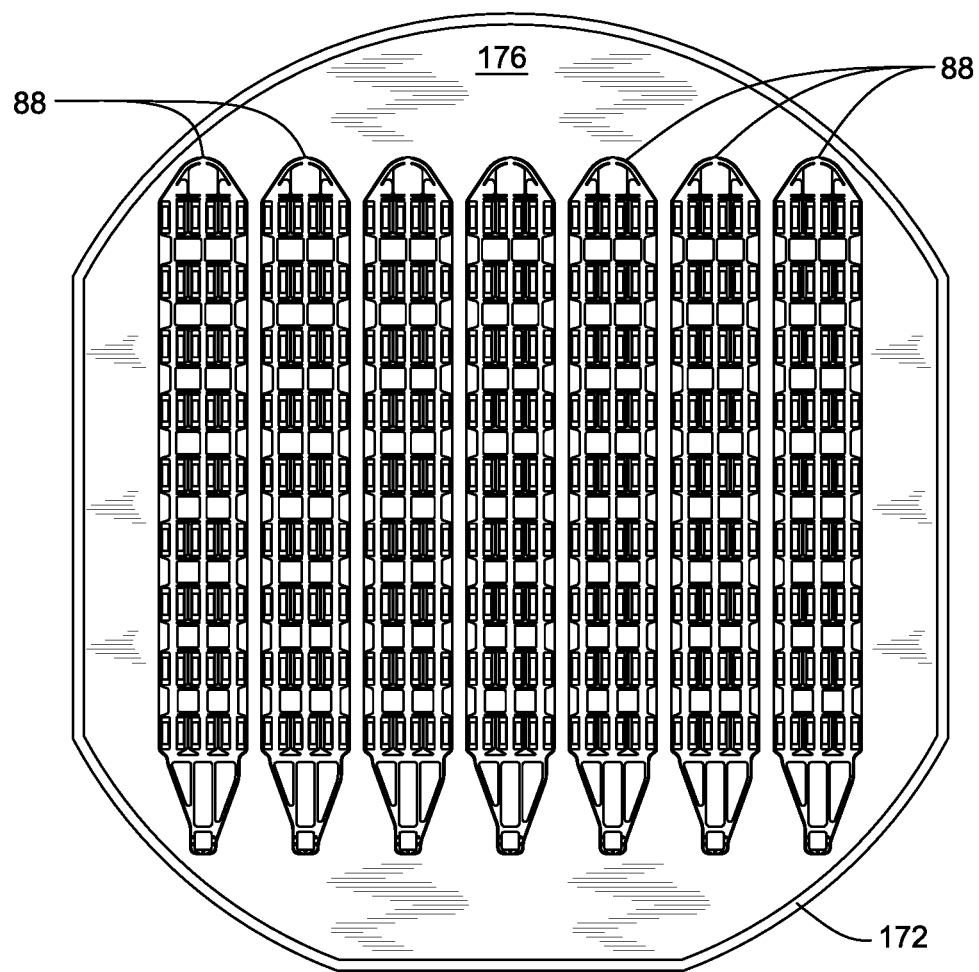
FIG. 14 is a plan view of the individual frames disposed over the LCP coupon on which the electrode array passive side layers are formed.

As a result of the lifting off of the remnants of the frame coupon 160 from the LCP coupon 176, the partially assembly arrays appear as in FIGS. 14 and 15. The plural frames 88 are bonded to the LCP coupon 176. FIG. 15 represents a section of one frame 88. More particularly, FIG. 15 is a cross section through a single tab 120 adjacent beams 124 of a single frame 88. The tab opening 122 it is observed is disposed over an underlying section of the frame forming LCP coupon 176. Owing to the placement of the frames 88 on the LCP coupon 176, each one of the LCP coupon slots 184 and 186 is located below and between the frame tab 120 and an adjacent frame beam 124.

Figure 16:
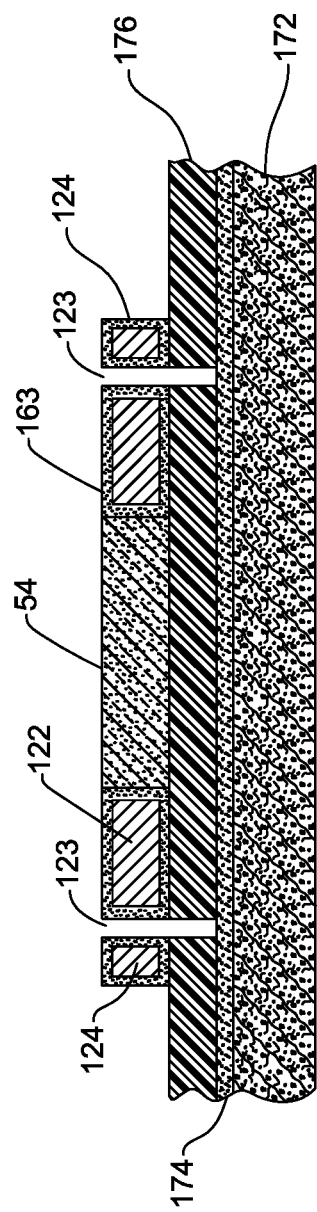
FIG. 16 is a cross sectional view of the frame and LCP coupon of FIG. 15 after a control module has been seated in the frame.

As represented by FIG. 16, the next step in the batch assembly of the electrode arrays 50 is the placement of the control modules 54 in the tab openings 122. The oxide coating 163 disposed around the window-defining faces of each frame 88 electrically insulates the control modules 54 from the frame.

Figure 17:
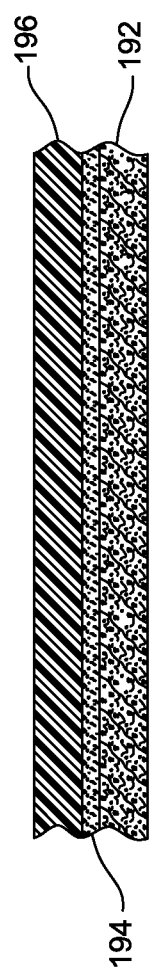
FIG. 17 is a cross sectional view of an LCP coupon from which array first intermediate LCP layers is formed immediately after the coupon is bonded to a backing.
Figure 18:
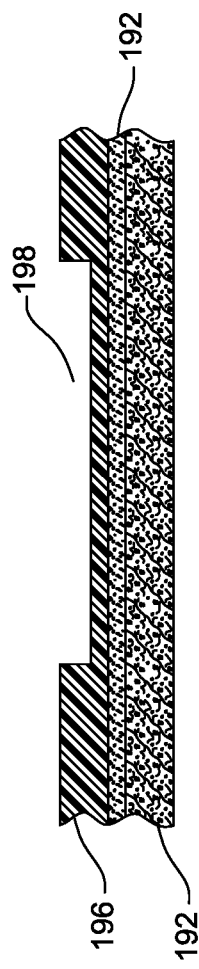
FIG. 18 is a cross sectional view of the LCP coupon of FIG. 17 showing the coupon after a recess has been formed to extend partially through the coupon.

Prior to the first intermediate LCP layers, LCP layers 138, being applied over the frames 88, these layers 138 are fabricated a LCP coupon, coupon 196 in FIG. 17. LCP coupon 196 is formed from the same material as LCP coupon 176. LCP coupon 196 has a thickness of 75 to 150 microns. To process LCP coupon 196, coupon 196, like coupon 176, is placed on a backing, backing 192 in FIG. 17. An adhesive layer, layer 194 holds LCP coupon 196 to backing 192. The same processes used to affix LCP coupon 176 to backing 172 are used to affix LCP coupon 196 to backing 192. Accordingly these process steps will not be redescribed. It should likewise be understood that these process steps are used to secure below described LCP coupons 224, 244, and 266 to, respectively, backings 220, 240, and 262.

After LCP coupon 196 is attached to backing 192, plural recesses 198 are formed in the coupon 196. Each recess 198 does not extend all the way through coupon 196. Instead each recess 198 extends inwardly from the outer surface of the coupon to a depth at least equal to the thickness of the frames 88. Recesses 198 are formed in LCP coupon 196 by first masking over the portions of the coupon 196 on which the recesses are not to be formed. Then, using the oxygen plasma RIE process, recesses are formed in the unmasked portions of the coupon 196. The aluminum mask is then removed. As seen best in FIG. 21, each recess 196 has an outline with a shape identical to the perimeter of the frame 88 over which the coupon 196 will subsequently be disposed. In terms of dimensions each recess 196 has a surface area that, at a minimum, corresponds to the surface area of the frame 88 subsequently fitted in the recess. Recesses 196 have a depth that, at a minimum, is equal to the thickness of the frames 88.

After recesses 198 are formed in LCP coupon 196, the coupon is subjected to a second oxygen plasma RIE process. This etching process is executed to form a number of openings. These openings, seen in FIG. 19, extend from the base of the recesses 198 completely through the rest of the LCP coupon 196. A number of these openings are slots, represented by slots 202 and 210 in FIGS. 19 and 21 and slots 212 in FIG. 21. Upon assembly of the arrays 50, these slots 202, 210 and 212 slots become part of the array slots 70 and 76. Specifically, slots 202 and 210 are different sections of a single one of the array I-shaped slots 70. Each slot 212 becomes a part of an array slot 76.

In this second etch process, a second set of openings, through bores 204, 206 and 208 are also formed in the LCP coupon 196. Each through bore 204 is generally circular in cross section and has a diameter of between 5 to 1000 microns and often 50 to 250 microns.

The next step in the fabrication of the plural first intermediate LCP layers 138 is the filling of through bores 204, 206 and 208 with conductive material as seen by FIG. 20. Metal, often gold, is deposited in through bores 204, 206 and 208. In one process for depositing this gold, first a thin layer of titanium, approximately 500 Angstroms thick is applied by a sputtering process over the whole of the coupon 196. This titanium adheres to the inner cylindrical walls of the LCP coupon 196 that define the bores 204, 206 and 208. A gold layer, also of approximately 1000 Angstroms thick, is then applied by a sputtering process to the whole of the coupon 196 over the titanium. It should be appreciated that this titanium layer is initially applied because titanium adheres well to both LCP and gold.

Once the thin gold layer is applied, gold is then plated only in bores 204, 206 and 208. To perform this plating, the coupon is masked so that only bores 204, 206 and 208 are exposed. The gold is then applied by an electroplating process so as to file the bore. In this process, the previously applied gold functions as a seed layer to which the electroplated gold bonds. The gold covered mask layer is removed. Then the thin layers of titanium and gold that cover the rest of the coupon are removed.

As will be apparent from the following description, the metal in bores 204 functions as the array vias 146 between the control module and conductor 56. The metal cores in bores 206 function as sections of the array vias 148 that extend between the control module and conductor 58. The metal cores in bores 208 function as sections of the array vias 150 that extend between the control module 54 and the overlying electrode 52. In FIG. 20, these metal cores are identified using the identification numbers of the vias that they eventually become.

Figure 21:
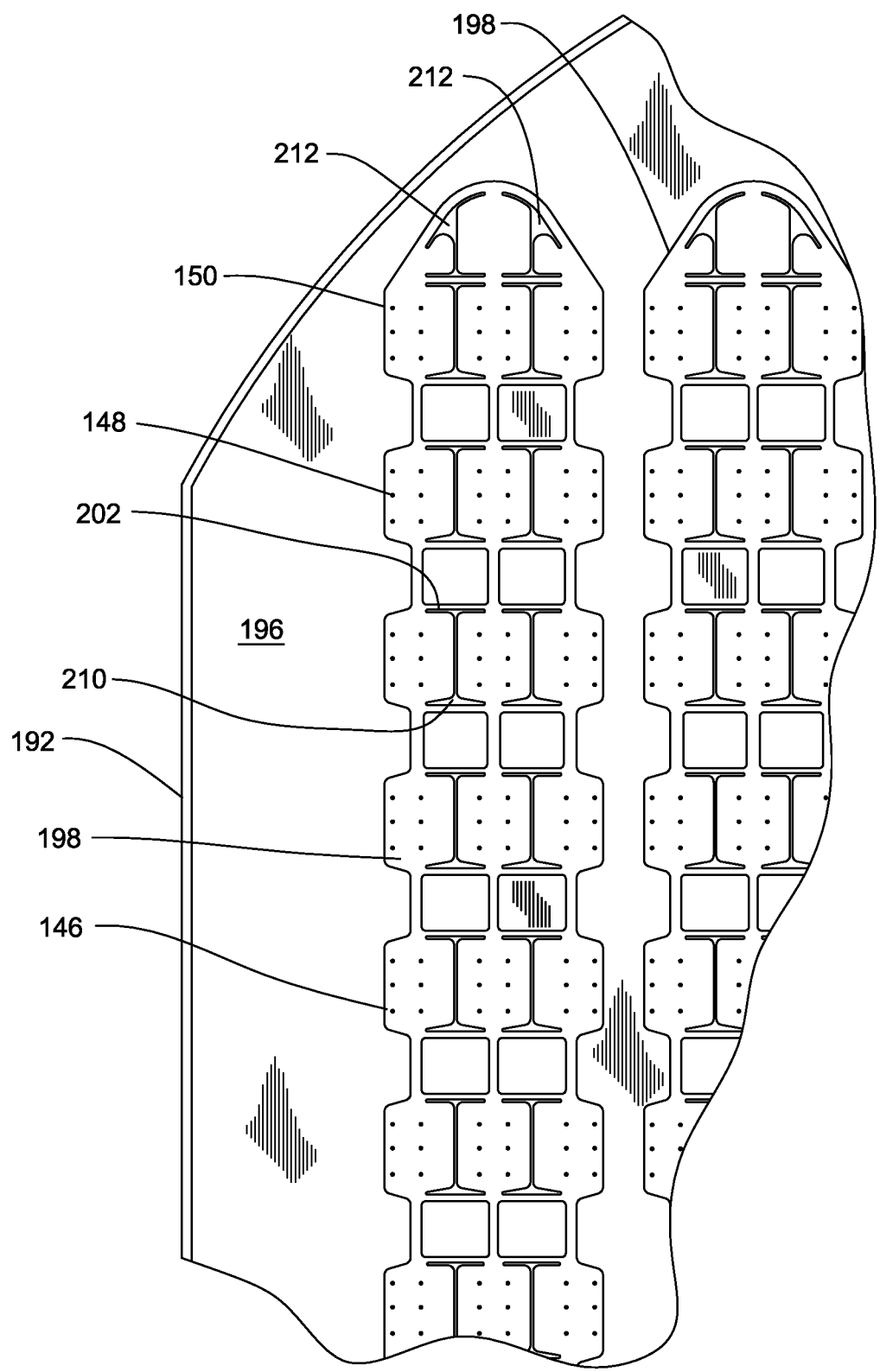
FIG. 21 is a plan view of the LCP coupon of FIG. 20 showing the plural recesses and slots formed in the coupon as well as the metal cores that extend through the coupon.

With the addition of the via-forming metal, LCP coupon 196 appears as in FIGS. 20 and 21. Specifically, the coupon 196 has a number of recesses 198. Each recess 198 is shaped to receive a separate frame 88. A number of slots 202 210 and 212, extend from the base of each recess 198, through the polymer, to the opposed face of the coupon 196, the face bonded to the adhesive layer 194. The slots correspond to sections of the array slots. Specifically, each pair of slots 202 and 210 is part of one of the array I-shaped slots 70. Slots 212 are part of the slots 76 located in the array head. Plural metal columns, each represented in FIG. 21 by a black dot, extend from the base of each recess 198 to the opposed face of the coupon 196.

Figure 22:
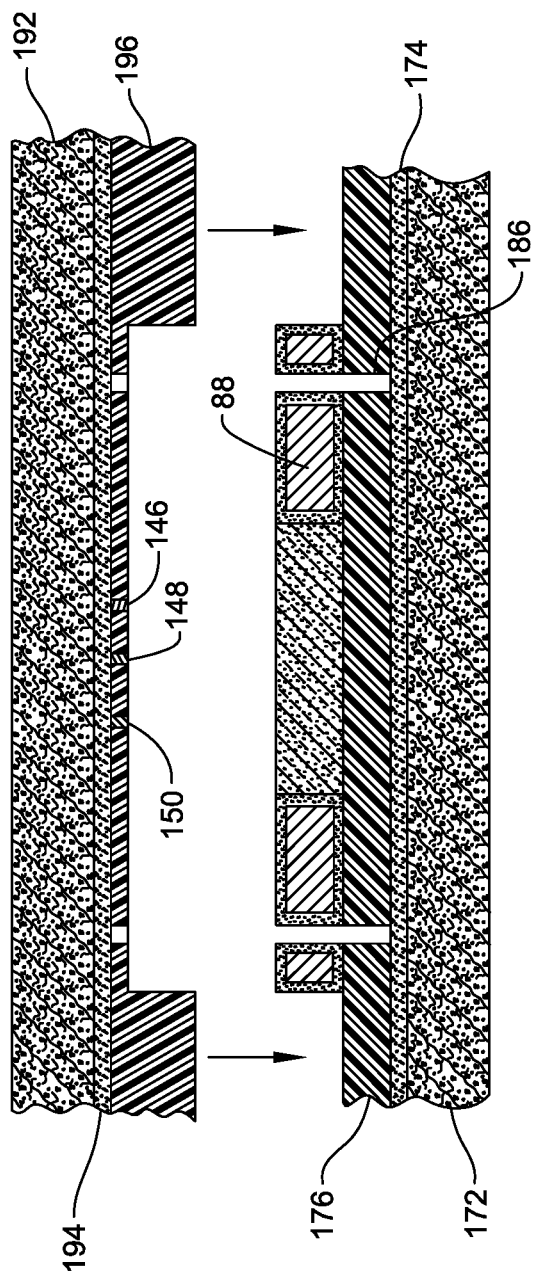
FIG. 22 is cross sectional view of how the LCP coupon of Figures and 19 and 20 is placed in registration over the LCP coupon and frame assembly of FIG. 15.

Once LCP coupon 196 is formed to define the plural LCP intermediate layers 138, the coupon 196, while still attached to backing 192 is inverted (step not shown). The inverted coupon 196 is then placed in registration over LCP coupon 176. More specifically as seen in FIG. 22, the two coupons 176 and 196 are aligned so that each recess 198 of coupon 196 is in registration over one of the frame 88.

Figure 23:
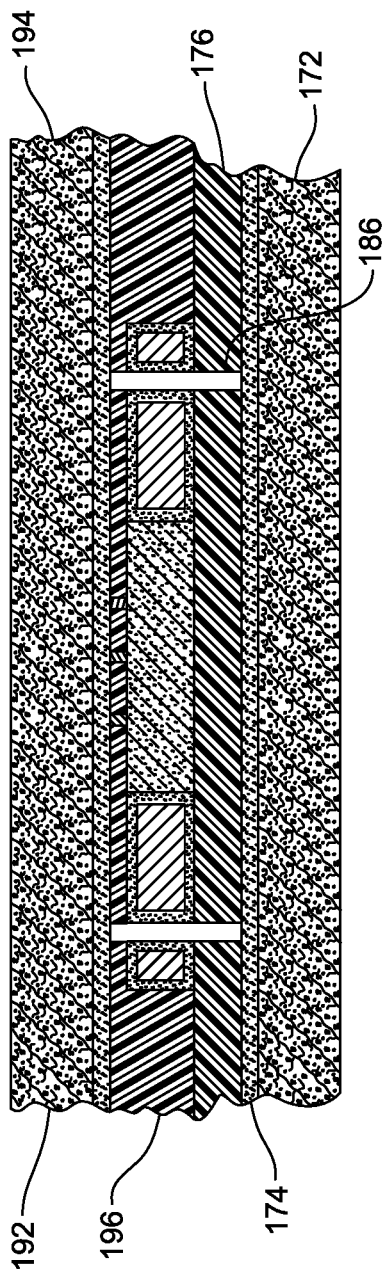
FIG. 23 is a cross section view of the bonded LCP coupons of FIG. 22.

The LCP coupon 196 is then placed against LCP coupon 176 as seen by FIG. 23. In this step, the frames 88 and the control modules 54 fitted in the frames, seat in the recesses 198. The outer surfaces of LCP coupons 176 and 196 abut. It should be appreciated that, as result of where the via forming metal columns are present in the LCP coupon 196, these metal columns seat over and abut the bond pads of the control modules 54. (Control module bond pads not illustrated.)

During these steps of inverting LCP coupon 196 and positioning the coupon 196 over coupon 176 it should be appreciated that the chuck that it is positioning the coupon 196 is actually holding onto backing 192.

Once the LCP coupons 176 and 196 are pressed together, the coupons are bonded together by a thermally induced pressure bond. In this process the LCP on the faces of the opposed coupons 176 and 196 become semi-liquid and adhere together to form a unitary structure. For purposes of understanding the invention, these plural LCP coupons, and, by extension, plural array LCP layers, are illustrated as separate layers.

After the LCP coupons 176 and 196 are bonded together, backing 192 is lifted off of LCP coupon 196. This process is performed by placing the assembly in an empty bath so that backing 192 is exposed down, against the base of the bath. The bath is filled with a sufficient volume of acetone to cover backing 192 but below the backing 172. The assembly is allowed to sit in the acetone until the acetone dissolves adhesive layer 194. Typically this takes anywhere from 10 to 30 minutes. As a result of the dissolving of the adhesive layer, the assembly, minus backing 192 can then be removed from the bath. Acetone remaining on the assembly is then removed by rinsing the assembly in isopropyl alcohol. The assembly is then subjected to a drying process. This process is performed by placing the assembly in a sealed oven, flooding the oven with nitrogen gas and raising the oven temperature to 80° C. The heat causes the acetone to evaporate off the assembly.

Figure 24:
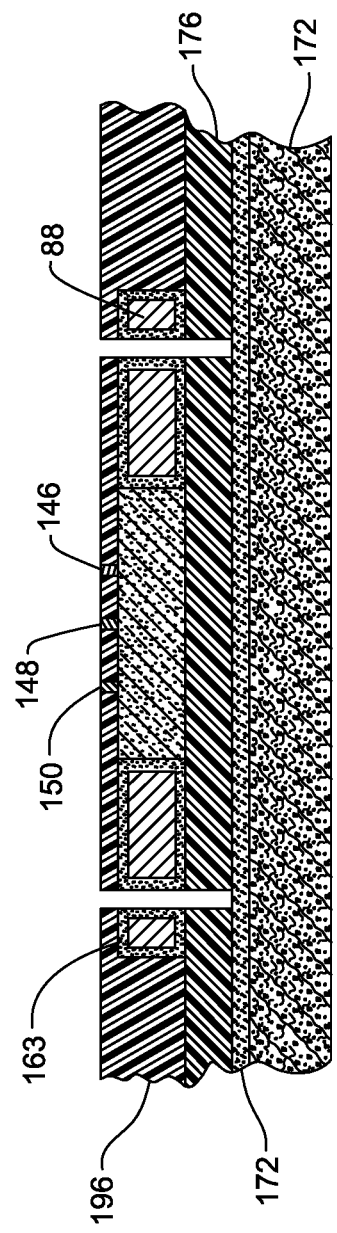
FIG. 24 is a cross sectional view of the bonded LCP coupons of FIG. 23 after the backing attached to the topmost LCP coupon has been removed.

Once the assembly is removed from the oven, the assembly appears as depicted in FIG. 24. The control modules 54 and frames 88 are embedded between the coupons that form LCP coupons 176 and 196. LCP coupon 176, the coupon forming layers 136, remains bonded to backing 132. The portions of vias 146, 148 and 150 that extend through the LCP coupon 196 extend through this coupon.

Figure 25:
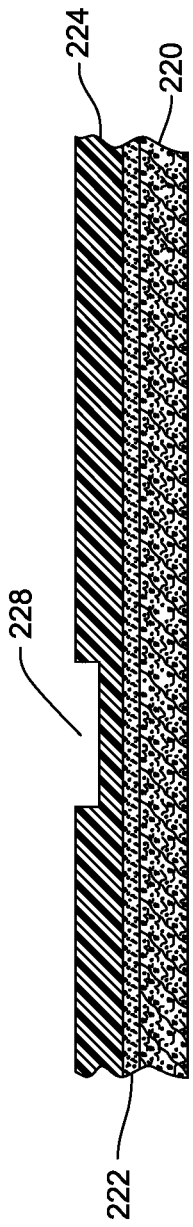
FIGS. 25, 26 and 27 are a sequence of cross sectional views depicting the shaping of the LCP coupon on which plural array second intermediate LCP layers are fabricated.

An LCP coupon, coupon 224, in FIG. 25, is shaped to form the plural second intermediate LCP layers 140. Coupon 224 has a thickness of between 10 and 50 microns. The previously described bonding steps are used to secure coupon 224 to its complementary backing, backing 220 in FIG. 25. Here it can be seen that adhesive layer 222 holds LCP coupon 224 to backing 220. LCP coupon 224 has a thickness of 10 to 50 microns. Not shown is the depiction of LCP coupon 224 after it is thermal compression bonded to the backing 220. As this drawing would essentially be the same as FIG. 17 which shows LCP coupon 196 after being press bonded to backing 192, this drawing is omitted.

After LCP coupon 224 is bonded to backing 192, a series of grooves 228 (one shown) are etched in the exposed face of the coupon. Grooves 228 are formed on the LCP coupon 224 so as to have the pattern of the conductors 56. Grooves 228 are formed using the etching steps used to form recesses 198 in LCP coupon 196. The grooves 228 are formed to have a depth of 5 to 15 microns relative to the exposed face of the LCP coupon 224. Grooves 228 have a generally rectangular cross sectionals shape.

Figure 26:
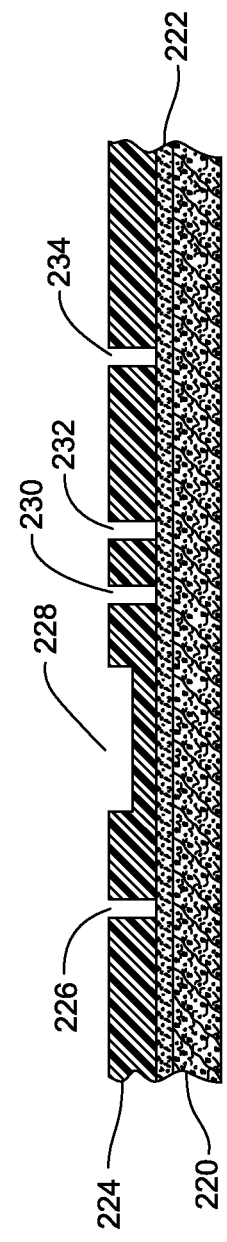

LCP coupon 224 is also shaped to form a number of openings seen in FIG. 26. One type of opening formed in LCP coupon are slots, represented by slots 226 and 234. The slots are sections of the array slots 70 and 76. Thus, coupon slots 226 and 234 are each different sections of what upon complete assembly of the array 50 is one of the I-shaped slots 70. Slot sections 226 and 234 of LCP coupon 224 are essentially identical to slot sections 202 and 210 of LCP coupon 196.

The second type of openings formed in LCP coupon 224 are the openings through which the conductors forming sections of vias 148 and 150 extend. In FIG. 26, these openings are through bores 230 and 232. Through bores 230 and 232 are thus analogues to, respectively, through bores 206 and 208 formed in LCP coupon 196. Bores 230 and 232 have the same shape and cross sectional dimensions as, respectively, bores 296 and 208.

In a series of steps, metal is first deposited in bores 230 and 232 and then in grooves 228. Initially a titanium adhesion layer and gold seed layer are deposited over the whole of the coupon 224. These layers have the same thickness as the previously described versions of these layers. Then a photo resist mask is placed over the LCP coupon 224. The only portions of the coupon 224 left exposed by this mask are the openings into bores 230 and 232. An electroplating process is then used to fill bores 230 and 232 with gold. The next step in this process is the removal of this first mask. A second mask is then applied to coupon 224. This mask is applied so as to leave exposed the outlines of the grooves 228. The coupon 224 is then subjected to a second electroplating process. In this process, gold is applied to fill the grooves 228. Upon completion of this electroplating process, the mask and underlying gold and titanium layers are removed. Here it should be understood that first electroplating process is performed to ensure that the gold rises to the top of the bores 230 and 232. The second electroplating process is performed to ensure that the face of the plated gold in the grooves 226 is essentially uniform with the exposed face of the LCP coupon 224.

Figure 27:
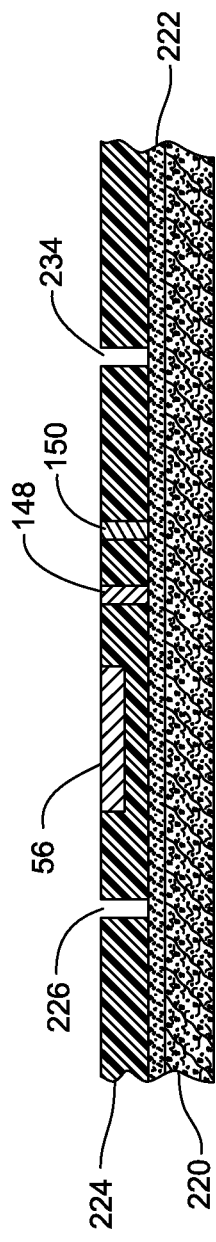
Figure 28:
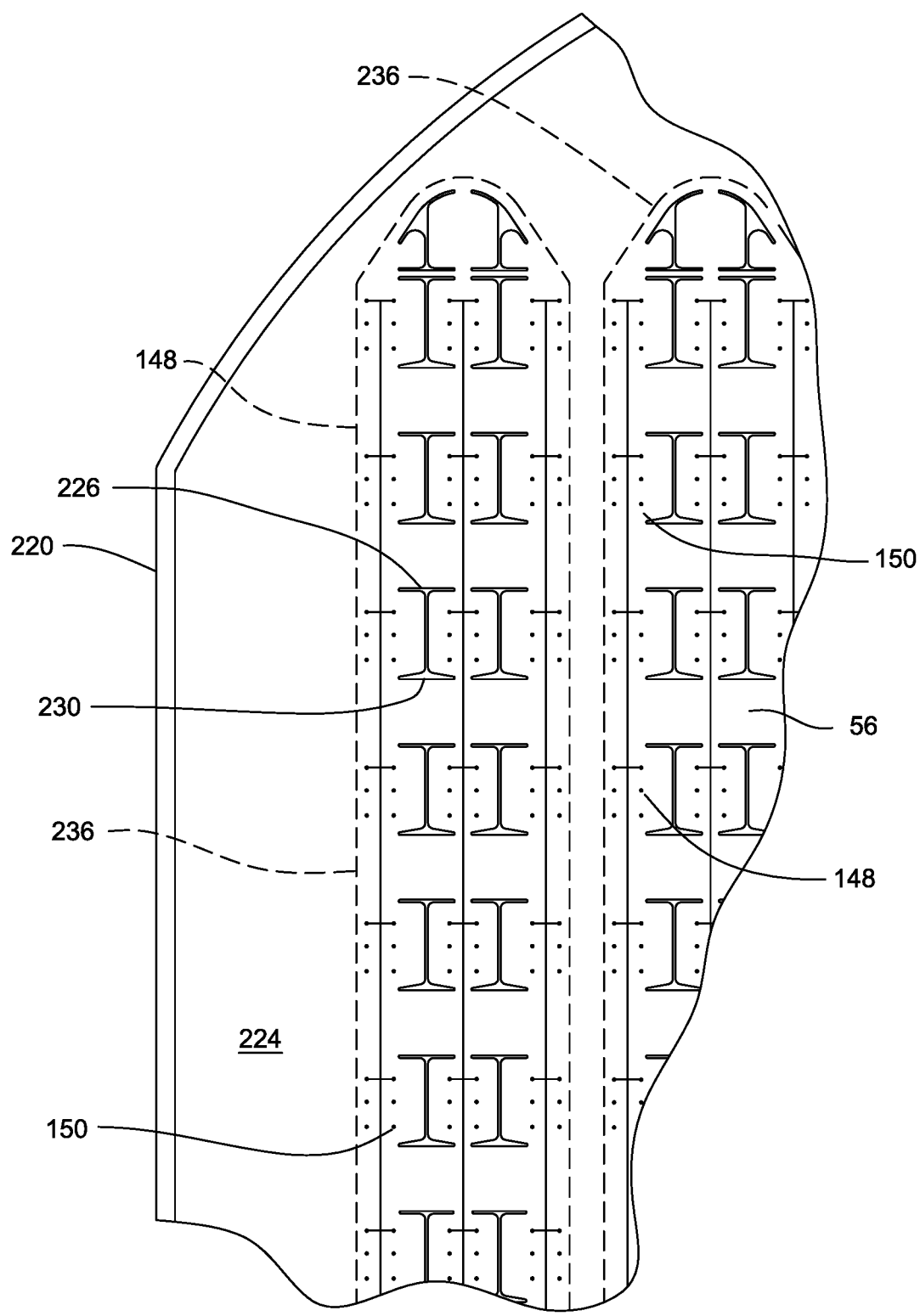
FIG. 28 is a plan view of the LCP coupon of FIG. 27.

As a consequence of the selective plating of the coupon 224, the coupon appears as in FIGS. 27 and 28. The gold fills grooves 228. These gold stripes are the conductors 56 and are identified as such. Gold cores are disposed in bores 230 and 232. These cores are sections of vias 148 and 150 and are identified as such. FIG. 28 depicts the exposed face of LCP coupon 224. The face of LCP coupon 224 is planar since it will abut the exposed planar face of LCP coupon 196. Dashed lines 236 are on the face of the LCP coupon 224 represent the perimeters of the individual LCP intermediate sections 140 eventually formed by different sections of the coupon. Within each section of the LCP coupon 224 defined by one of the boarders there are three primary branches of conductor 56. Branches extend from a trunk conductor not illustrated but also formed on the defined section of the LCP coupon 224. A number of secondary branch conductors extend off each primary branch. Also shown in within the defined sections of LCP coupon 224 are plural pairs of dots. These dots represent the heads of the partially formed vias 148 and 150.

Once LCP coupon 224 is fabricated the coupon, while still attached to backing 220, is inverted. LCP coupon is positioned over LCP coupon 196. Specifically, LCP coupon is positioned so that: LCP coupon 224 slot sections 226 and 234 are in registration of LCP coupon 196 slot sections 202 and 210; conductors 56 in registration over vias 146; and via sections 146 and 150 of LCP coupon 224 and in registration with the corresponding via sections in LCP coupon 176. The same process steps used to bond LCP coupon 196 to LCP coupon 176 is used to bond LCP coupon 224 to LCP coupon 176. As the steps for inverting and positioning and bonding LCP coupon 196 are essentially identical to the same process steps used to bond LCP coupon 176, illustrations of these steps are not repeated.

Figure 29:
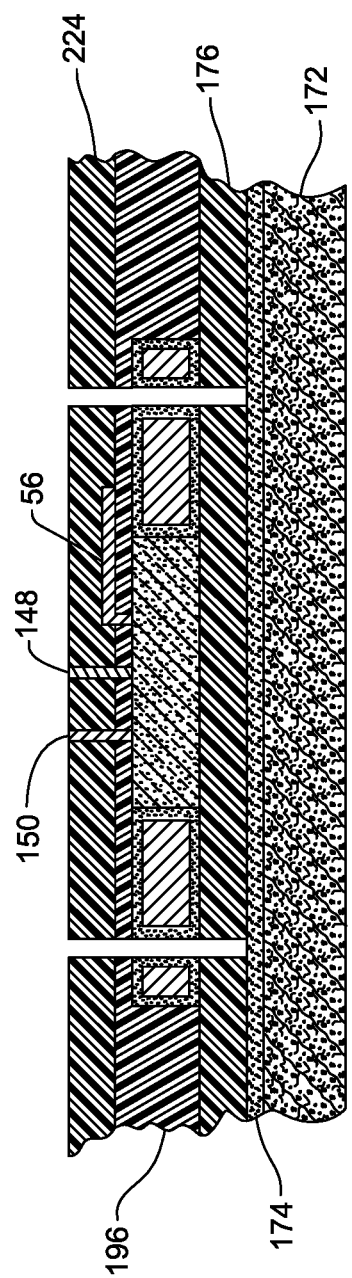
FIG. 29 is a cross sectional view of a portion of a partially assembled electrode array being assembled according to the process of this invention after the LCP layer of FIGS. 27 and 28 is bonded to the assembly of FIG. 24.

Once LCP coupon 224 is bonded to LCP coupon 196, backing 220 is lifted off of coupon 224. The same process steps used to remove backing 192 off of coupon 196 are used to lift off backing 220. At the end of these process steps, a number of partially assembled electrode arrays 50 are disposed on backing 172. FIG. 29 illustrates a portion of one such array 50. Here, control module 54 is disposed in a frame tab 120. The tab 120 and adjacent beams 124 are disposed between LCP coupons 176 and 196 that, respectively, form layers 136 and 138. The LCP coupon 224 that forms the plural second intermediate LCP layers 140 is disposed over LCP coupon 196.

Figure 30:
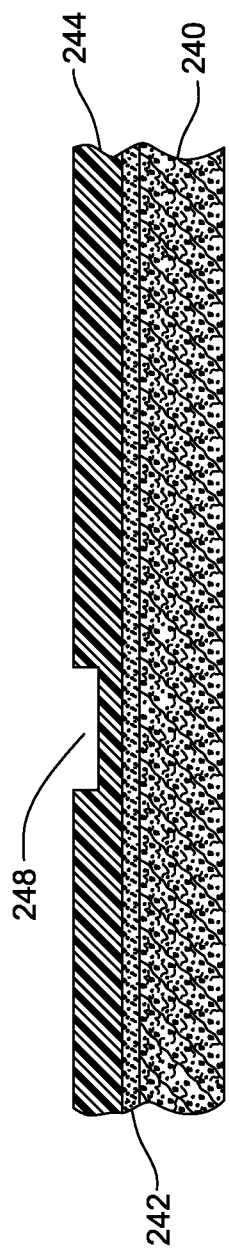

An LCP coupon 244, seen in FIG. 30, is then subjected to processing to form plural third intermediate LCP layers 142. LCP coupon 24 has a thickness similar to that of coupon 224. Initially. LCP coupon 244 is bonded to a backing 240 using the previously described LCP-to-backing bonding steps. While not illustrated, after these bonding steps it should be understood that the resultant structure is similar if not identical to the backing 172 and LCP coupon assembly of FIG. 17. A layer of adhesive, layer 242, holds coupon 244 to backing 240.

Plural grooves 248, one seen in FIG. 30, are then formed in LCP coupon 244. Grooves 248 are essentially identical in cross sectional geometry and in width and depth dimensions to grooves 228 integral with LCP coupon 244. Grooves 248 are the void spaces internal to the LCP coupon 244 in which the metal forming array conductors 58 is subsequently be deposited. The grooves 248 are therefore formed in LCP coupon 244 in the locations where the conductors 58 need to be present.

Once grooves 248 are formed in LCP coupon 244, plural openings, illustrated best in FIG. 31, are formed in the coupon. Some of these opens are slots. These slots are sections of the slots 70 and 76 that extend through the individual array. In FIG. 31, slot sections 246 and 252 are illustrated. Slot sections 246 and 252 are portions of one of the I-shaped slots 70 that extends through the array.

The other type of openings formed in LCP coupon 244 are through bores 250 (one shown). Through bores 250 receive the deposits of metal that, upon formation of the arrays 50 becomes portions of the vias 150.

Once the openings are formed in the coupon, the metal is deposited in the grooves 248 and bores 250. The same process steps used to deposit metal in the grooves 228 and bore 230 and 232 of LCP coupon 224 are used to deposit metal in grooves 248 and bores 250 of LCP coupon 224. The results of the depositing of this metal are depicted in FIG. 32. The metal deposited in grooves 248 will function as the conductors 58 and is therefore identified as such. The metal cores that form in bores 250 function as sections of the vias 150 and are identified as such.

Once LCP coupon 244 is fabricated the coupon, while still attached to backing 240, is inverted. LCP coupon 244 is positioned over LCP coupon 224. Specifically, LCP coupon 244 is positioned so that: LCP coupon 224 slot sections 246 and 252 are in registration of LCP coupon 224 slot sections 226 and 234; conductors 58 in registration over vias 148; and via sections 256 off LCP coupon 244 and in registration with via sections 238 in LCP coupon 224. The same process steps used to bond the other LCP coupons together are employed to bond LCP coupon 244 to LCP coupon 224. As the steps for inverting and positioning and bonding LCP coupon 196 are essentially identical to the previously described LCP inverting, positioning and bonding steps illustrations of these steps are not repeated.

Figure 33:
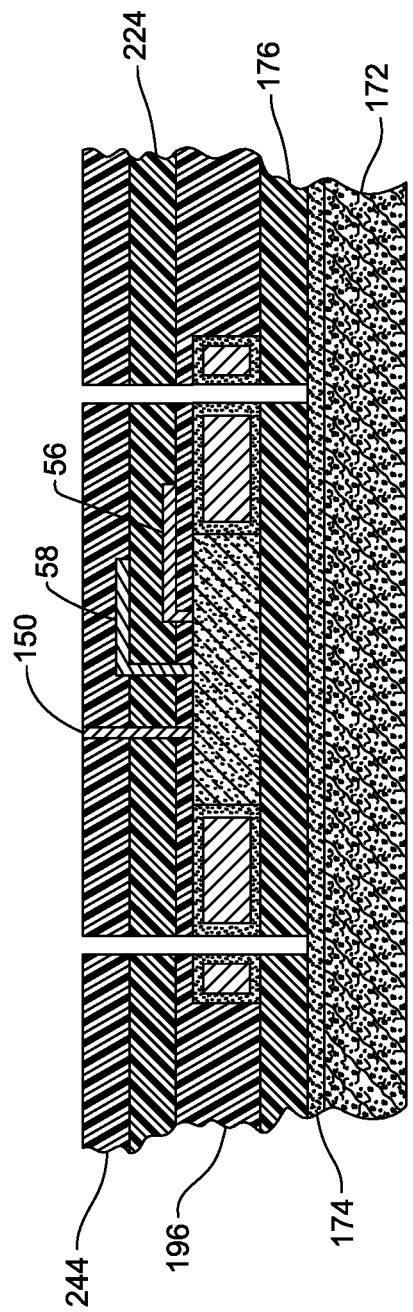
FIG. 33 is a cross sectional view of a partially assembled electrode array being assembled according to the process of the invention after the LCP layer of FIG. 32 is bonded to the assembly of FIG. 29.

Backing 240 is then lifted off LCP coupon 244 using the previously described backing lift off process. At this time, the partially assembled electrode arrays 50 remain bonded to backing 172. As seen by FIG. 33, the partially assembled electrode arrays at this time include an LCP layer not present in the partially assembled array of FIG. 29. Specifically, the LCP coupon 244, which forms the third intermediate LCP layers 142 is now disposed over coupon 224, the coupon forming the second intermediate LCP layers 140. Embedded in the LCP layers 142 are the conductors 58 and portions of the vias 150.

Figure 34:
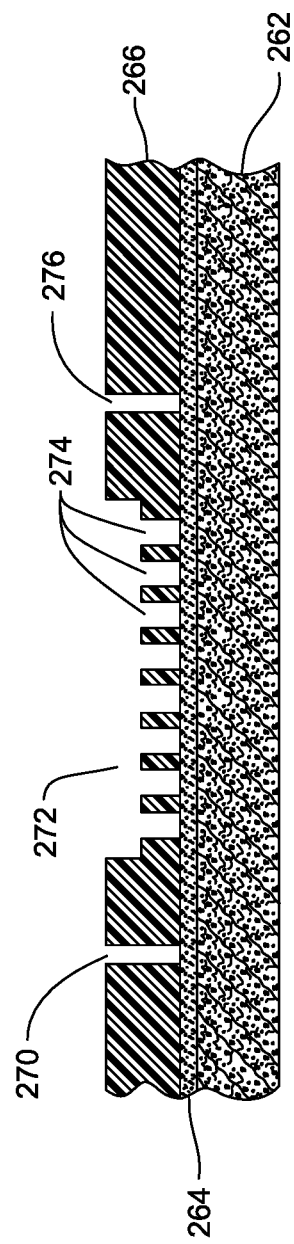
FIGS. 34 and 35 cross sectional views depicting the shaping of the LCP coupon on which plural array active side LCP layers are formed.

An LCP coupon 266, seen in FIG. 34, is shaped to form the plural active side LCP layers 144. Coupon 266 is at least 50 microns thick. To facilitate the processing of coupon 266, the coupon is first bonded to backing 262 by adhesive layer 264.

Once the LCP coupon 266 is fixed to backing 262, plural rectangularly shaped recesses and openings are formed in the coupon as depicted in FIG. 34. These recesses and openings are formed in plural oxygen plasma RIE processes. In a first oxygen plasma reactive ion etching process slots are formed in the coupon 266 to extend completely through the coupon. In FIG. 34 these slots are represented by slots 270 and 276. Upon assembly of each array 50, the through slots 270 and 276 become sections of the slots 70 and 76 that extend through the array. In the second etching process, rectangular recesses 272, one shown, are formed in LCP coupon 266. Each recess 272 functions as the void space wherein, in a subsequent step, metal forming the base pad of each electrode 52 is deposited. Thus, in the second etching process, the recesses 272 are formed so as to have a shape and dimensions that correspond to the shape and dimensions of the array electrodes 52. Recesses 276 are formed so as to have a depth of approximately 5 to 40 microns. The third oxygen plasma RIE process is executed to form through openings 274 that extend downwardly from the bases of the recesses 270. Each through opening 274 has a diameter of between 10 to 300 microns and is typically circular in cross-sectional shape. Each through opening 274 extends from the base of the recess 266 from which the opening extends to the opposed face of the coupon 266, the face bonded to backing 262.

Figure 35:
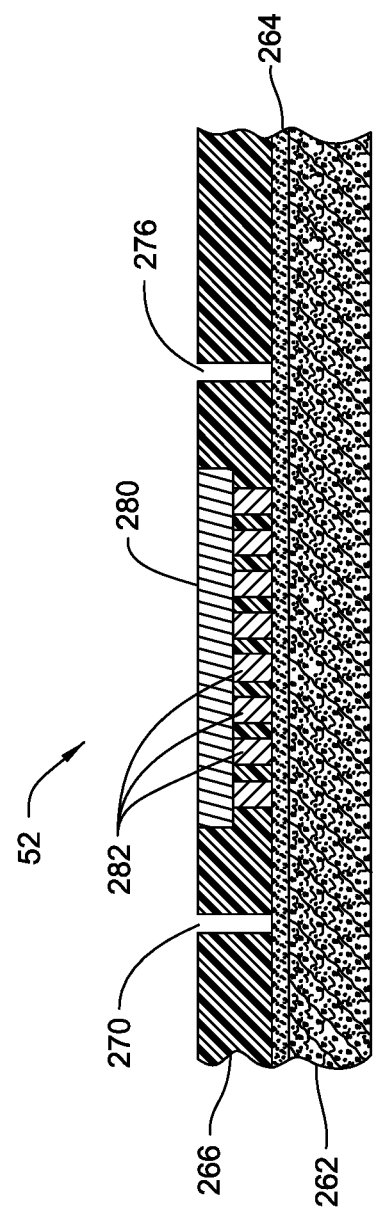

Metal is then deposited in recesses 272 and openings 274 to form the electrodes 52. An initial step in this process is the masking of the coupon 266. The only sections of the coupon left mask-free are the openings into through openings 274. Iridium is then deposited by a sputter process into the through openings 274. The iridium is not, however, deposited to fill the whole of the openings 274. Instead, the iridium is deposited only partially fills the openings from the face of the coupon 266 disposed against backing 262. The top 5 to 10 microns of each opening 274 is not filled. Then, while the mask remains in place, titanium is sputter deposited on the coupon 266 to fill the openings 274. Each through opening thus includes a column of metal, the lower portion of which is iridium, the upper section of which is titanium. Each of these metal columns is considered a button 282 of the electrode 52 with which the column is integral. In FIG. 35, where an electrode is illustrated, the plural layers of metal forming each button 282 are not illustrated.

Once the electrode buttons 282 are formed the first mask is removed. A titanium adhesion layer approximately 500 Angstroms thick is applied over the whole of the LCP coupon 266. A gold seed layer, of the same thickness as the titanium adhesion layer, is the applied over the titanium layer. A second mask is then applied to the coupon 266. The only sections of the coupon 266 left exposed by the second mask are the openings into the recesses 272. Gold is then electroplated to the LCP coupon 266 to fill the recesses. The mask and the gold and titanium disposed underneath the mask are then removed.

Upon removal of the mask, gold and titanium, the electrodes 52 can be considered fabricated. One electrode 52 is seen in FIG. 35. The electrode includes a gold base pad 280, the gold in the recess LCP coupon has the recess 272. A number of buttons 282 extend from the base pad through the LCP underlying the base pad to the exposed face of the polymer coupon 266. The exposed faces the iridium cores that form the buttons 282 are the actual exposed surfaces of the electrode 52. Buttons are formed to have iridium faces because iridium provides a good low impedance interface against the living tissue against which the array 50 is disposed. The titanium sections of buttons 282 are present because the titanium adheres well to iridium, liquid crystal polymer and gold.

Figure 36:
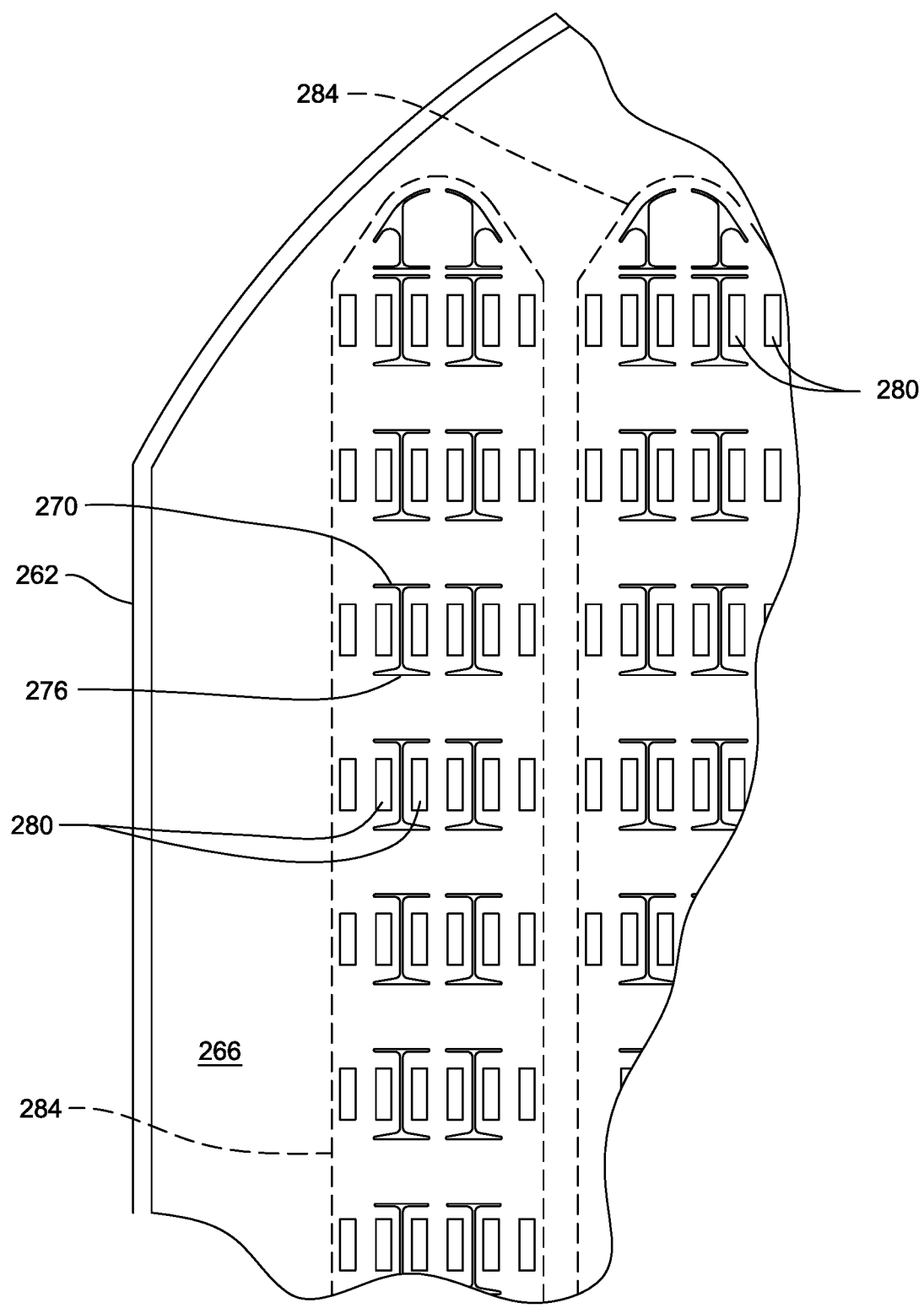
FIG. 36 is a plan view of the LCP coupon of FIG. 35.

The LCP coupon 266 thus appears as depicted in FIG. 36. In FIG. 36 dashed lines 284 identify the perimeters of the array active side LCP layers 144 formed by the coupon 266. The face of the coupon 266 is planar. A number of slots extend through the coupon 266. In FIG. 36 only two slot sections, slot sections 270 and 276 are identified. Upon manufacture of the array 50, these slots become sections of the array slots 70 and 76. Also visible on the exposed face of LCP coupon 266 are the exposed surfaces of the electrode base pads 280.

After the LCP coupon 266 is shaped and the metal layers deposited, the coupon 266 is bonded to the exposed face of LCP coupon 224. While still attached to backing 262, LCP coupon 266 and positioned over LCP coupon 224. LCP coupon 266 is positioned against LCP coupon 224 so that the gold base pad 280 of each electrode 52 is disposed against the exposed face of the complementary via 150. LCP coupon 266 is then bonded to LCP coupon 224 by the previously described thermal induced compression bonding process. As a consequence of this bonding, vias 150 bond to the base pads 280 of the overlying electrodes 56. Backing 262 is then lifted off from LCP coupon 266 using the previously described backing lift off process. At this stage in the process of assembling the plural electrode arrays 50, an array in cross section would appear in the assembled state depicted in FIG. 2.

At this stage in the electrode array assembly process, the plural electrode arrays 50 remain bonded to backing 172. The arrays 50 are each part of a laminate structure formed by the stacked LCP coupons 176, 196, 224, 244 and 266. Prior to removal of the electrode arrays from the backing 172, cuts are made in the LCP laminate to separate the arrays from the surrounding sections of the laminate. These cuts are made by a press.

Once the arrays 50 are defined on the backing 172, the arrays are removed from backing and surrounding remnant LCP laminate. This step is performed by using the previously described backing lift off process to dissolve the adhesive 174 holding the arrays to the backing. The arrays are then dried, cleaned and tested for use.

Post manufacture of the electrode array assembly 50 there are substantial portions of the assembly that consist of the stacked layers of LCP film, layers 136, 138, 140, 142 and 144 that are stacked one on top of the other. There are no electrical components, conductors or support members are disposed between these layers. These LCP film laminates form the form the body of the array that projects from the frame 88. Portions of this body can be considered membranes that extend over the sections of the array in which the frame 88 is embedded. Returning to FIG. 1A, two such membranes, membranes 302 are the LCP film laminate sections that extend between longitudinally adjacent spaced apart frame tabs 120 that extend outwardly from frame bridges 114 and 118. In FIG. 1A dashed lines outline portions of the frame 88 disposed within the LCP film laminate body of the array. Other membranes, membranes 304, extend in the rectangular spaces between the bridges 114, 116, 118 and beams 124.

Also while not show it should be appreciated that within frame slots 123 and 132 the adjacent LCP layers 136 and 140 overlap the frame slots by at least 25 microns. These LCP layers cover the exposed interior side edges of the frame 88.

As mentioned above the frames 88 internal to each array 50 may have been shaped prior to their bonding to LCP coupon 176. If the frames 88 were so shaped, each frame 88 upon lift off of the associated array returns to its pre-flattened non-planar shape. This causes the array 50 with which each frame 88 is integral to develop a shape that generally corresponds to that of the array.

This invention thus provides a means to assembly small implantable electrode arrays out of a liquid crystal polymer. This material is thin, flexible and able to support electrical components. Moreover, in comparison to other polymers, liquid crystal polymer is less prone to absorb water. Each of these features makes liquid crystal polymer well suited as a substrate or superstrate material for devices such as electrode arrays intend for implantation against or into living tissue.

This invention also does more than provide a means to assemble electrode arrays out of liquid crystal polymer. The invention provides a means to simultaneously batch assembly plural arrays out of this polymer. This ability to batch assemble plural arrays assists in reducing the costs of the manufacture of these arrays.

III. Alternative Embodiments

The method of forming an assembly of this invention is described with reference to the fabricated assembly being an electrode array. It should be understood that this method of fabricating assemblies that include thin polymer support layers of this invention may be used to fabricate medical assemblies other than electrode arrays that provide either a therapeutic benefit or diagnostic information. Also, while the invention is described as a means for assembling medical devices, that is implanted in living tissue, use of this invention is not so limited. The invention may also be employed to construct medical devices intended for skin or surface tissue attachment.

Likewise, the invention need not only be employed to construct medical devices. Such devices include but are not limited to: transducers for biological or mechanical sensing; display panels; circuit assemblies that, post fabrication need to have non-planer shapes. Likewise, while the disclosed assemblies contain plural thin polymer layers, the method of this invention may be used to fabricate assemblies that have only a single layer of polymer. In versions of the invention not intended for biological or medical use, it may not be necessary to employ a biocompatible polymer as the polymer that forms the device support layer.

Likewise, while many electrode arrays fabricated according to this invention will have plural electrodes, the method of this invention is not limited to fabricating electrode arrays with plural electrodes. The method of this invention may be used to fabricate an electrode assembly that only has a single electrode.

Similarly, the method of this invention may be used to assembly devices that do not include many features of the described electrode arrays. For example a device assembled according to this invention may not have frame or frame members that provide some stiffness to the assembled device. Devices assembled according to this invention may have stiffening members different from the described single piece frames 88. For example, the frame may consist of a number of structural members that are not connected to each other. This type of frame may be desirable when the end goal is the fabrication of a device that has some sections that are relatively flexible and other sections that have less flexibility.

It should similarly be appreciated that the devices assembled employing this method may include components that provide a therapeutic benefit and/or diagnostic information that are not electrically conductive. For example, the device may include structural members that resist compression. These versions of the device may function as stents. Still other versions of the device may include components that are embedded with a pharmaceutical agent. Once the device is implanted in the living tissue, the pharmaceutical agent is released.

Likewise, the material from which the frame members are formed may be different than the disclosed Nitinol. Thus, if it is desirable that the frame members be less elastic or less, flexible plastic or metals other than Nitinol may be used as frame members.

This invention may be used to fabricate electrical devices that include integrated circuits and discrete components that are directly mounted to a surface of one of the polymer layers. In these versions of the invention, it may be necessary to form openings in the exposed surface of the polymer support layer prior to mounting the component that provided the therapeutic benefit or diagnostic information to the support layer.

Similarly, it should be appreciated that the described order of the process steps is exemplary, not mandatory. For example, in an optimal version of this invention, it would most likely be best to first shape the frame coupon 160 and the LCP coupons 176, 196, 224, 248 and 266 before assembling the coupons together to form the laminate assembly. Likewise, the sequence of the steps performed to shape the individual LCP coupons may vary from what has been described. For example, if an LCP coupon is to include layers that contain both through slots and conductors the following sequence of steps may be used to fabricate the coupon. First the through openings and or grooves and recesses in which the conductive material is to be deposited is formed. Then, the conductive material is deposited in these openings, grooves and/or recesses. After these processing steps any additional openings that extend either partially or completely through the LCP coupon are formed. These sequence of processing steps may be performed if it is technically efficient to, prior to the forming of any openings or recesses in which metal is not to be deposited, mask the deposited metal.

Similarly, the metal may be deposited on the LCP coupons using processes different from what has been disclosed. For example, a different process from what has been described above with respect to FIGS. 35 and 36 may be used to form the electrodes. In this process, the iridium cores are deposited in the coupon through openings 274 in the steps described above. The mask covering the coupon 266 is then removed. Once the mask is removed, titanium is sputtered over the whole of the coupon 266, this titanium, which is applied to a thickness of 5 to 10 microns and more often 7 to 9 microns, fills the unfilled portions of the coupon openings 274. This titanium also coats the surfaces of the liquid crystal polymer forming the bases of the recesses 272. A seed layer of gold approximately 500 Angstroms thick is deposited over the whole of the titanium layer. The coupon 266 is masked so as to cover the coupon except the openings into the recesses 272. Gold is then sputter deposited over the coupon so as to form the electrode base pads 282.

Also, there may be versions of the invention wherein it is desirable to first attach at least some of the functional components to the support layer. After these components are attached, the components that increase the rigidity of the layer, the Nitinol frame, or similar stiffening component, is attached to the layer.

Similarly other means may be employed to define the individual electrode arrays 50 on the backing that serves as the primary backing upon which the arrays are built. In the Figures, this is backing 172. For example, in one alternative version of the invention, instead of cutting away the unused sections of the LCP laminate from around the arrays, these portions of the laminate may be etched away.

Figure 37:
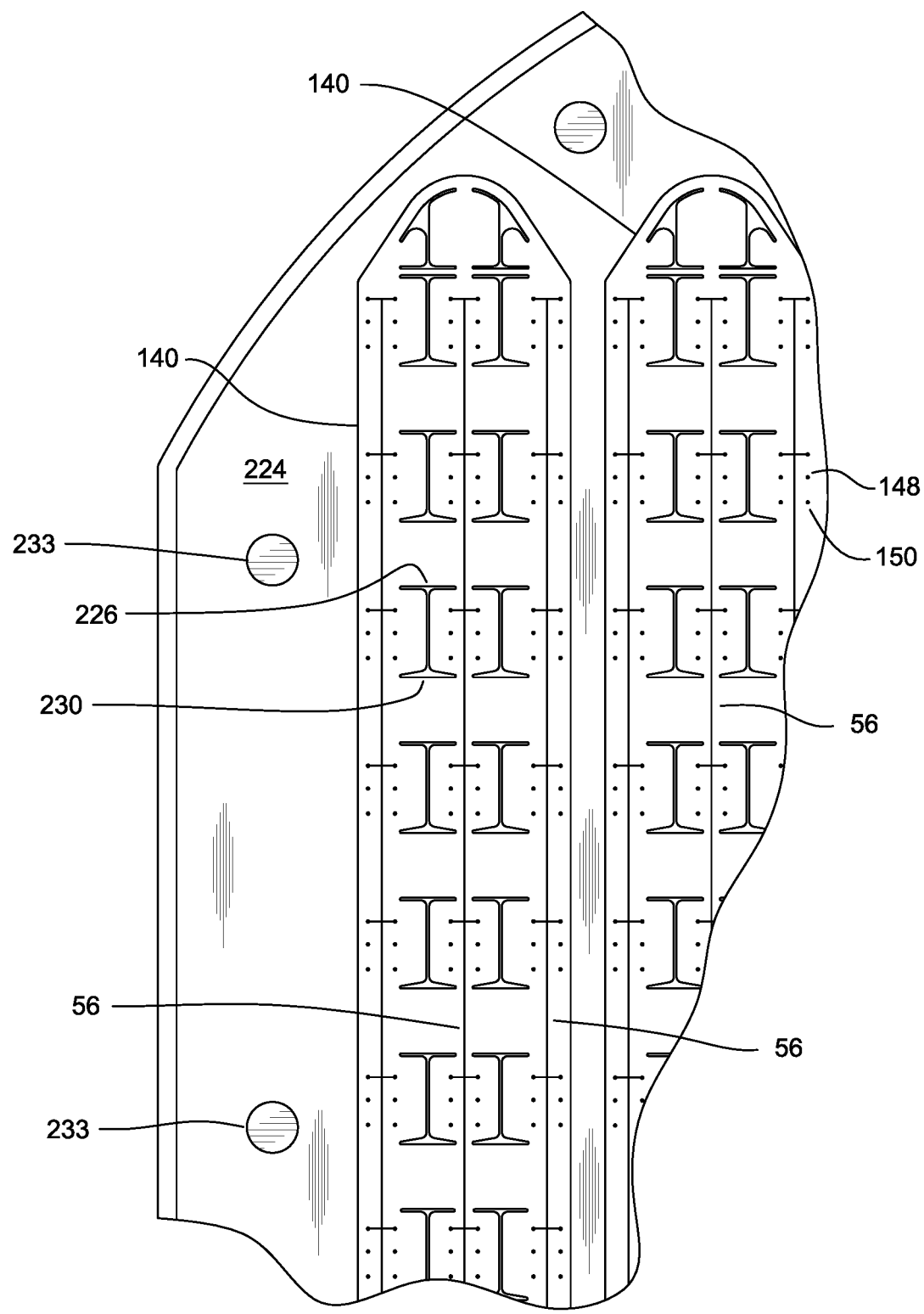
FIG. 37 is a plan view of, as result of an alternative manufacturing process of this invention, the arrangement of plural separate array-forming LCP layers on a common backing.

Likewise, in some versions of the invention, the steps of shaping each LCP coupon to define features of the individual array LCP layers may further include the shaping of the coupon to define the outer perimeters of the LCP layers. Once this shaping is performed, disposed on each once the coupon are plural spaced apart LCP layers. This is depicted in FIG. 37. This depicts what one would see if LCP coupon 224 where fabricated according to this process. Here, instead of the whole of the coupon being attached to backing 220, the plural spaced apart, fully formed second intermediate LCP layers 140 are bonded to the backing 220. Also left of the backing after the LCP etching process are LCP pads 233. The pads 233 are spaced from the LCP layers 140. During the subsequent LCP layer-to-LCP layer bonding process, the pads 233 first abut and then bond to like LCP pads that extend upwardly from the underlying backing 172. This pad-against-pad abutment prevents excessive flexure of the backings during the bonding process.

The invention is described for use in fabricating assemblies formed out of polymer layers having a thickness of 1 mm or less. In described version of the invention, the polymer layers have thickness of 500 microns or less. While the invention is described as being very useful for fabricating assemblies out of thin film liquid crystal polymer the method of this invention is not so limited. The invention may be used to fabricate an assembly on flexible substrates or superstrates that are thicker than the above described LCP sheets. Likewise the assembly may be used to fabricate assemblies on support layers such as substrates or superstrates formed from material other than liquid crystal polymer. Biocompatible polymers include in this class of materials include silicone, parylene, polyamide and polymers other than liquid crystal polymers. Devices wherein the biocompatible support layer is a thin film composite structures that include one or more polymer components may also be constructed using the method of this invention. These composites, in addition to polymer, include material such as silicon and metal. It should likewise be appreciated that this invention may be used to manufacture assemblies wherein the polymer support layers are formed from different types of polymers.

Likewise there is no requirement that in all versions of the invention pressure bonding be employed to bond the multi-layer forming polymer coupons together. Depending on the device being fabricated and the material forming the polymer coupons, biocompatible adhesives may be used to bond the coupons together. This adhesive may or may not be pressure set.

Further, the device assembled according to this invention may not be a complete device. The device assembled according to this invention may be a sub-assembly of a device that includes additional components.

Accordingly, it is an object of the appended claims to cover all such variations and modifications that come within the true spirit and scope of this invention.

What is claimed is:

1. A medical device for implantation on or in a living being to provide a therapeutic benefit and/or offer diagnostic information, the medical device comprising:
   a first polymer layer being flexible;
   a second polymer layer being flexible and being bonded to the first polymer layer;
   wherein the first and second polymer layers each comprise a maximum thickness of 1 mm and each comprise liquid crystal polymer provided in a cured sheet form prior to being bonded;
   a control module comprising an integrated circuit and being sandwiched between the first and second polymer layers;
   at least one electrode coupled to one or more of the polymer layers; and
   at least one conductor extending from the control module to the at least one electrode through one or more of the polymer layers.

2. The medical device of claim 1, wherein at least one of the polymer layers comprises a biocompatible material.

3. The medical device of claim 1, wherein the polymer layers comprise a common shape formed by cutting or etching.

4. The medical device of claim 1, wherein the control module is electrically conductive.

5. The medical device of claim 1, wherein the control module provides rigidity to the medical device.

6. The medical device of claim 1, wherein the control module is elastic.

7. The medical device of claim 1, wherein each polymer layer has a cross-section thickness, the cross-section thicknesses of the polymer layers being different from each other.

8. The medical device of claim 1, wherein the polymer layers are formed from the same polymer.

9. The medical device of claim 1, wherein at least one of the polymer layers comprises a slot for receiving the control module.

10. The medical device of claim 1, further comprising a third polymer layer being flexible and being bonded to at least one of the first and second polymer layers.

11. The medical device of claim 10, wherein the third polymer layer comprises a biocompatible material.

12. The medical device of claim 1, further comprising a stiffening component disposed between the polymer layers.

13. The medical device of claim 12, wherein the stiffening component is elastic.

\* \* \* \* \*